United States Patent [19]

Browne

[11] Patent Number: 5,428,160

[45] Date of Patent: Jun. 27, 1995

[54] SUBSTITUTED IMIDAZO[5-A]PYRIDINE DERVIATIVES AND OTHER SUBSTITUTED BICYCLIC DERIVATIVES

[75] Inventor: Leslie J. Browne, Morris Plains, N.J.

[73] Assignee: Ciba-Geigy Corporation, Ardsley, N.Y.

[21] Appl. No.: 632,584

[22] Filed: Dec. 21, 1990

Related U.S. Application Data

[60] Continuation of Ser. No. 419,922, Oct. 11, 1989, abandoned, which is a continuation of Ser. No. 120,283, Nov. 13, 1987, Pat. No. 4,889,861, which is a division of Ser. No. 825,830, Feb. 4, 1986, Pat. No. 4,728,645, which is a continuation of Ser. No. 747,195, Jun. 20, 1985, abandoned, which is a continuation-in-part of Ser. No. 622,421, Jun. 20, 1984, Pat. No. 4,617,307, and a continuation-in-part of Ser. No. 451,902, Dec. 21, 1982, Pat. No. 4,588,732.

[51] Int. Cl.6 .................. C07D 417/04; C07D 471/04; C07D 491/04
[52] U.S. Cl. ..................................... 544/61; 544/125; 544/362; 546/121
[58] Field of Search ................... 546/121; 544/61, 125, 544/362

[56] References Cited

U.S. PATENT DOCUMENTS

| | | | |
|---|---|---|---|
| 4,228,291 | 10/1980 | Durant et al. | 548/138 |
| 4,409,226 | 10/1983 | Bristol | 424/256 |
| 4,444,775 | 8/1984 | Ford | 424/256 |
| 4,617,307 | 10/1986 | Browne | 546/121 |

OTHER PUBLICATIONS

J. of Med. Chem. Vol. 16 (1973) 1272–1276.
Tetrahedron vol. 37 Suppl. 1981 pp. 191–200.

*Primary Examiner*—Johann Richter
*Attorney, Agent, or Firm*—Norbert Gruenfeld

[57] ABSTRACT

Disclosed are compounds of formula I

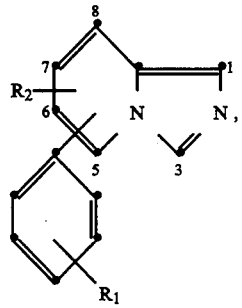

wherein $R_1$ represents hydrogen, lower alkyl, substituted lower alkyl, nitro, halogen, free, etherified or esterified hydroxy, free, etherified, oxidised etherified or esterified mercapto, unsubstituted, mono- or disubstituted amino, ammonio, free or functionally modified sulfo, free or functionally modified formyl, $C_2$–$C_{20}$-acyl, cyano, free or functionally modified carboxy; and $R_2$ represents hydrogen, lower alkyl, substituted lower alkyl, halogen; free, etherified or esterified hydroxy; free, etherified, oxidised etherified or esterified mercapto; free or functionally modified carboxy, or acyl; the 7,8-dihydro derivatives thereof; and compounds of the formula I*

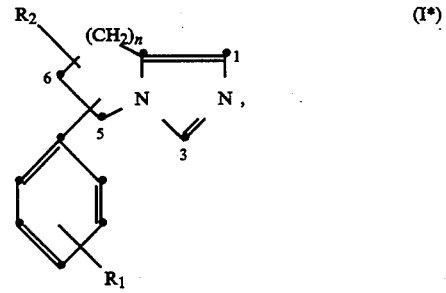

wherein n denotes 0, 1, 2, 3, or 4, and $R_1$ and $R_2$ are as defined above under formula I and salts thereof; e.g. as aromatase inhibitors; pharmaceutical compositions containing these compounds; the use of these compounds for the treatment of conditions responsive to e.g. aromatase inhibition in mammals; processes and intermediates for preparing these compounds.

4 Claims, No Drawings

SUBSTITUTED IMIDAZO[5-A]PYRIDINE DERVIATIVES AND OTHER SUBSTITUTED BICYCLIC DERIVATIVES

REFERENCE TO RELATED APPLICATIONS

This application is a continuation of application Ser. No. 07/419,922 filed Oct. 11, 1989 (now abandoned), which is a continuation of application Ser. No. 07/120,283 filed Nov. 13, 1987, U.S. Pat. No. 4,889,861 which is a division of application Ser. No. 06/825,830, filed Feb. 4, 1986, now U.S. Pat. No. 4,728,645, which is a continuation of application Ser. No. 06/747,195 filed Jun. 20, 1985 (now abandoned) which is a continuation-in-part of application Ser. No. 06/622,421 filed Jun. 20, 1984, now U.S. Pat. No. 4,617,307, and which is also a continuation-in-part of application Ser. No. 06/451,902 filed Dec. 21, 1982, now U.S. Pat. No. 4,588,732.

SUMMARY OF THE INVENTION

The invention relates to substituted imidazo[1,5-a]pyridine derivatives and other substituted bicyclic derivatives which have valuable pharmacological properties e.g. as aromatase inhibitors, to pharmaceutical compositions containing these compounds, to the use of these compounds for the treatment of conditions responsive to e.g. aromatase inhibition by administration of an effective amount of said compounds or compositions to mammals including man, to processes for preparing these compounds, to intermediates and to processes for preparing these intermediates.

DETAILED DESCRIPTION OF THE INVENTION

Particularly, the invention relates to the substituted imidazo[1,5-a]pyridine derivatives of the formula I

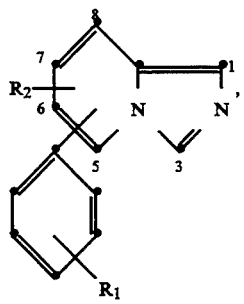

(I)

wherein $R_1$ represents hydrogen, lower alkyl, substituted lower alkyl, nitro, halogen, free, etherified or esterified hydroxy, free, etherified, oxidised etherified or esterified mercapto, unsubstituted, mono- or disubstituted amino, ammonio, free or functionally modified sulfo, free or functionally modified formyl, $C_2$–$C_{20}$-acyl, cyano, free or functionally modified carboxy; and $R_2$ represents hydrogen, lower alkyl, substituted lower alkyl, halogen; free, etherified or esterified hydroxy; free, etherified, oxidised etherified or esterified mercapto; free or functionally modified carboxy, or acyl; the 7,8-dihydro derivatives thereof; and compounds of the formula I*

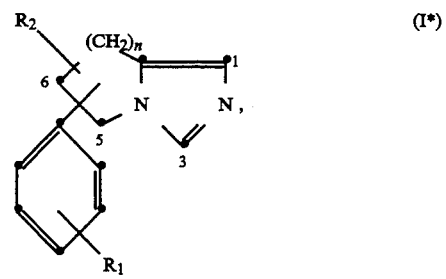

wherein n denotes 0, 1, 2, 3 or 4, and $R_1$ and $R_2$ are as defined above under formula I, in a compound of formula I* it being possible for the two substituents $C_6H_4$-$R_1$ and $R_2$ to be attached to any of the saturated carbon atoms of the saturated ring, either both to the same carbon atom or to different carbon atom; stereoisomers, mixtures of these stereoisomers; or pharmaceutically acceptable salts thereof.

The term "lower" means that groups so designated usually contain up to and including 7, and preferably up to and including 4, carbon atoms.

The compounds of formula I* as well as certain 7,8-dihydro derivatives of formula I contain at least one asymmetric carbon atom. They can be found as R- or S-enantiomers as well as enantiomeric mixtures thereof, such as a racemate. The present invention is intended to include all these forms, also those further isomers, and mixtures of at least two isomers, for example a diastereoisomeric mixture or enantiomeric mixture, which become possible if one or more further asymmetric center(s) are present within the molecule.

Lower alkyl is e.g. n-propyl, isopropyl, n-butyl, isobutyl, sec-butyl or tert-butyl, also n-pentyl, isopentyl, neopentyl, n-hexyl, isohexyl or n-heptyl, but preferably ethyl and especially methyl.

Substituted lower alkyl $R_1$ is preferably substituted by hydroxy, etherified hydroxy, such as lower alkoxy, esterified hydroxy, such as lower alkanoyloxy, acyl, such as lower alkanoyl, amino, mono- or disubstituted amino, such as lower alkylamino or di-lower alkylamino, halogen, preferably fluoro, free or functionally modified sulfo, preferably sulfo or sulfamoyl, or free or functionally modified carboxy, such as carboxy, lower alkoxycarbonyl, carbamoyl; or cyano.

Substituted lower alkyl $R_2$ is preferably substituted by aryl or free or functionally modified carboxy, especially carboxy or lower alkoxycarbonyl.

Halogen is e.g. bromo or iodo, preferably fluoro and especially chloro.

Etherified hydroxy is especially lower alkoxy, also, for example, aryloxy or aryl-lower alkoxy. Esterified hydroxy is e.g. acyloxy, preferably lower alkanoyloxy, but may also e.g. aroyloxy or lower alkoxycarbonyloxy.

Etherified mercapto is in particular lower alkylthio, also e.g. arylthio or aryl-lower alkylthio. Oxidised etherified mercapto is e.g. aryl-sulfinyl or aryl-sulfonyl and especially lower alkyl-sulfinyl or lower alkylsulfonyl. Esterified mercapto is e.g. acylthio, such as lower alkanoylthio.

Monosubstituted amino is in particular lower alkylamino, further e.g. arylamino, aryl-lower alkylamino or acylamino, especially lower alkanoylamino, but also e.g. aroylamino.

Disubstituted amino is in particular di-lower alkylamino, also lower alkyleneamino, oxa-, thia- or azalower alkyleneamino (in the latter of which the aza-nitrogen atom may be substituted e.g. by a hydrocarbon radical, such as lower alkyl), such as N-morpholino, N-thiomorpholino or optionally 4-lower alkylsubstituted N-piperazino.

Ammonio comprises e.g. quaternary ammonium salts derived from corresponding disubstituted amino groups mentioned above, which contain as quaternary substituent e.g. optionally substituted lower alkyl, preferably lower alkyl, hydroxy- or halo-lower alkyl or aryl-lower alkyl. Especially ammonio is tri-lower alkylammonio, such as trimethylammonio. The ammonium salts correspond to the salts defined hereinafter, especially the salts mentioned in particular as being pharmaceutically acceptable, non-toxic acid addition salts, and more especially to those salts formed with hydrohalic acids, sulfuric or phosphoric acid.

Free or functionally modified sulfo is e.g. sulfo ($-SO_3H$), esterified sulfo, such as lower alkoxysulfonyl, amidated sulfo, such as sulfamoyl, lower alkylsulfamoyl or di-lower alkylsulfamoyl, or sulfonyl halide, such as sulfonyl chloride; and is preferably sulfo or sulfamoyl.

Free or functionally modified formyl is preferably formyl or iminomethyl ($-CH=NH$) which may be N-substituted by free, etherified or esterified hydroxy, such as hydroxy, lower alkoxy or lower alkanoyloxy, by lower alkyl, aryl or amino; but may be also an acetal, such as a di-lower alkylacetal, e.g. dimethylacetal.

Acyl, usually containing 1-20 carbon atoms, is the corresponding radical of a carboxylic acid, preferably aroyl or halo-$C_2$-$C_7$-alkanoyl and especially lower alkanoyl. $C_1$-Alkanoyl corresponds to formyl.

Free or functionally modified carboxy is e.g. carboxy, esterified carboxy, preferably lower alkoxycarbonyl; amidated carboxy, preferably carbamoyl, lower alkylcarbamoyl, di-lower alkylcarbamoyl or hydroxycarbamoyl. Further comprised are 5-tetrazolyl or unsubstituted or lower alkylsubstituted 4,5-dihydro-2-oxazolyl.

Aryl, as such or within radicals like aryloxy, aryl-lower alkylthio, arylsulfonyl, arylamino etc., is e.g. 1- or 2-naphthyl, preferably phenyl which is substituted, especially monosubstituted, by e.g. lower alkyl, lower alkoxy and/or halogen, and is in particular phenyl. Aroyl, as such or within radicals like aroyloxy etc., is arylcarbonyl, in particular benzoyl.

Lower alkoxy is preferably methoxy or ethoxy, also e.g. n-propoxy, isopropoxy, n-butoxy, isobutyoxy or tert-butoxy.

Lower alkanoyloxy is e.g. formyloxy, acetoxy, propionyloxy or pivaloyloxy.

Lower alkanoyl is e.g. formyl, acetyl, propionyl or pivaloyl. Halo-$C_2$-$C_7$-alkanoyl is preferably trifluoroacetyl. Lower alkanoyl-amino is preferably acetylamino or propionylamino, but also e.g. formylamino.

Lower alkoxycarbonyl is preferably methoxycarbonyl or ethoxy-carbonyl. Lower alkoxycarbonyloxy is e.g. methoxycarbonyloxy or ethoxycarbonyloxy.

Lower alkylamino is e.g. methylamino, ethylamino, n-propylamino or isopropylamino. Di-lower alkylamino is e.g. dimethylamino, ethylmethylamino or diethylamino. Lower alkyleneamino contains e.g. from 2 to 7, preferably 4 to 6, ring carbon atoms and is, for example, N-pyrrolidino or N-piperidino.

Lower alkylthio is e.g. methylthio, ethylthio, n-propylthio or isopropylthio, while lower alkylsulfinyl is e.g. methylsulfinyl, and lower alkylsulfonyl is e.g. methylsulfonyl or ethylsulfonyl. Lower alkanoylthio is preferably formylthio or acetylthio.

Lower alkoxysulfonyl is e.g. methoxysulfonyl or ethoxysulfonyl. Lower alkylsulfamoyl is e.g. N-methyl- or N-ethylsulfamoyl, while di-lower alkylsulfamoyl is e.g. dimethyl- or diethylsulfamoyl.

Lower alkylcarbamoyl is e.g. N-methylcarbamoyl or N-ethylcarbamoyl, while di-lower alkylcarbamoyl is e.g. dimethyl- or diethylcarbamoyl.

The compounds of the invention form acid addition salts with acids, particularly pharmaceutically acceptable salts, with conventional acids, for example mineral acids, e.g. hydrochloric acid, sulfuric or phosphoric acid, or organic acids, for example aliphatic or aromatic carboxylic or sulfonic acids, e.g. formic, acetic, propionic, succinic, glycolic, lactic, malic, tartaric, citric, ascorbic, maleic, fumaric, hydroxymaleic, pyruvic, phenylacetic, benzoic, 4-aminobenzoic, anthranilic, 4-hydroxybenzoic, salicyclic, 4-aminosalicyclic, pamoic, gluconic, nicotinic, methanesulfonic, ethanesulfonic, halobenzenesuflonic, toluenesulfonic, naphthalenesulfonic, sulfanilic or cyclohexylsulfamic acid. Salts may also be formed with amino acids, such as arginine and lysine.

Compounds of the invention having acidic groups, for example a free carboxy or sulfo group, form especially metal or ammonium salts, such as alkali metal or alkaline earth metal salts, e.g. sodium, potassium, magnesium or calcium salts, as well as ammonium salts, which are formed with ammonia or suitable organic amines. There come into consideration for the salt formation especially aliphatic, cycloaliphatic, cycloaliphatic-aliphatic or araliphatic primary, secondary or tertiary mono-, di- or poly-amines, as well as heterocyclic bases, such as lower alkylamines, for example di- or tri-ethylamine, hydroxy-lower alkylamines, such as 2-hydroxyethylamine, bis-(2-hydroxyethyl)-amine or tris-(2-hydroxyethyl)-amine, basic aliphatic esters or carboxylic acids, e.g. 4-aminobenzoic acid 2-diethylaminoethyl ester, lower alkyleneamines, e.g. 1-ethylpiperidine, cycloalkylamines, e.g. dicyclohexylamine, benzylamines, e.g. N,N'-dibenzylethylenediamine, or bases of the pyridine type, e.g. pyridine, collidine or quinoline.

In the presence of several acidic or basic groups, mono- or poly-salts may be formed. Compounds of the invention having an acidic group and a basic group may also be present in the form of inner salts, i.e. in zwitterionic form, or a part of the molecule may be present in the form of an inner salt and another part in the form of a normal salt. The pharmaceutically acceptable salts mentioned hereinbefore are preferred. For isolation or purification it is also possible to use other salts than the therapeutically acceptable salts, for example the picrates.

Preferred are the compounds of formula I, wherein $R_1$ represents hydrogen, lower alkyl; lower alkyl substituted by hydroxy, lower alkoxy, lower alkanoyloxy, lower alkanoyl, amino, lower alkylamino, di-lower alkylamino, halogen, sulfo, carboxy, lower alkoxycarbonyl, carbamoyl or cyano; nitro, halogen, hydroxy, lower alkoxy, lower alkanoyloxy, phenylsulfonyloxy, lower alkylsulfonyloxy, mercapto, lower alkylthio, amino, lower alkylsulfonyl, lower alkylsulfonyl, lower alkanoylthio, amino, lower alkylamino, di-lower alkylamino, lower alkyleneamino, N-morpholino, N-thiomorpholino, optionally 4-lower alkylsubstituted N-piperazino, tri-lower alkylammonio, sulfo, lower alkoxysulfonyl, sulfamoyl, lower alkylsulfamoyl, di-lower alkylsulfamoyl, formyl; iminomethyl optionally N-substituted by hydroxy, lower alkoxy, lower alkanoyloxy, lower alkyl, phenyl or amino; $C_2$–$C_7$-alkanoyl, benzoyl, carboxy, lower alkoxycarbonyl, carbamoyl, lower alkylcarbamoyl, di-lower alkylcarbamoyl, cyano, 5-tetrazolyl, optionally lower alkylsubstituted 4,5-dihydro-2-oxazolyl or hydroxycarbamoyl; and $R_2$ represents hydrogen, lower alkyl, phenyl-lower alkyl, carboxy-lower alkyl, lower alkoxycarbonyl-lower alkyl, halogen, hydroxy, lower alkoxy, lower alkanoyloxy, mercapto, lower alkylthio, phenyl-lower alkylthio, phenylthio, lower alkanoylthio, carboxy, lower alkoxycarbonyl or lower alkanoyl; the 7,8-dihydro derivatives thereof; and compounds of the formula I*, wherein n denotes 0, 1, 2, 3 or 4; and $R_1$ and $R_2$ are as defined above for compounds of formula I; it being possible for the phenyl portion within the radicals phenylsulfonyloxy, phenyliminomethyl, benzoyl, phenyl-lower alkyl, phenyl-lower alkylthio and phenylthio to be unsubstituted or substituted by lower alkyl, lower alkoxy or halogen; and in a compound of formula I* it being possible for the two substituents $C_6H_4$-$R_1$ and $R_2$ to be attached to any of the saturated carbon atoms of the saturated ring, either both to the same carbon atom or to different carbon atoms; stereoisomers, mixtures of these stereoisomers; or pharmaceutically acceptable salts thereof.

Further preferred are the compounds of formula I, wherein $R_1$ represents lower alkyl, lower alkyl substituted by hydroxy, amino, di-lower alkylamino, by 1 to 5 fluorine atoms, by carboxy, lower alkoxycarbonyl, carbamoyl or cyano; nitro, halogen, hydroxy, lower alkoxy, amino, lower alkylamino, di-lower alkylamino, sulfo, sulfamoyl, formyl, iminomethyl; iminomethyl N-substituted by hydroxy, lower alkoxy, lower alkanoyloxy, lower alkyl or phenyl; carboxy, lower alkoxycarbonyl, carbamoyl, lower alkylcarbamoyl, di-lower alkylcarbamoyl or cyano; and $R_2$ is hydrogen, lower alkyl, lower alkoxy or halogen; or compounds of the formula I*, wherein n denotes 1, 2 or 3; $R_1$ is as defined above for the compounds of formula I and $R_2$ represents hydrogen, lower alkyl, phenyl-lower alkyl, carboxy-lower alkyl, lower alkoxycarbonyl-lower alkyl, halogen, lower alkoxy, lower alkylthio, phenyl-lower alkylthio, phenylthio, carboxy, lower alkoxycarbonyl or lower alkanoyl; in a compound of formula I* it being possible for the two substituents $C_6H_4$-$R_1$ and $R_2$ to be attached to any of the saturated carbon atoms of the saturated ring, either both to the same carbon atom or to different carbon atoms; stereoisomers, mixtures of these stereoisomers; or pharmaceutically acceptable salts thereof.

Especially preferred are the compounds of formula I, wherein $R_1$ represents lower alkyl, hydroxy-lower alkyl, halogen, amino, formyl, carboxy, lower alkoxycarbonyl, carbamoyl, N-lower alkylcarbamoyl or cyano; and $R_2$ is hydrogen; or the compounds of formula I*, wherein n denotes 1, 2 or 3; $R_1$ is as defined above for formula I and $R_2$ represents hydrogen, lower alkylthio, lower alkoxycarbonyl, phenyl-lower alkyl, carboxy-lower alkyl or lower alkoxycarbonyl-lower alkyl; in a compound of formula I* it being possible for the two substituents $C_6H_4$-$R_1$ and $R_2$ to be attached to any of the saturated carbon atoms of the saturated ring, either both to the same carbon atom or to different carbon atoms; stereoisomers, mixtures of these stereoisomers or pharmaceutically acceptable salts thereof.

The invention relates especially to compounds of formula I, wherein $R_1$ represents lower alkyl, hydroxy-$C_2$–$C_7$-alkyl; lower alkyl substituted by amino, di-lower alkylamino, by 2 to 5 fluorine atoms, by carboxy, lower alkoxycarbonyl, carbamoyl or cyano; nitro, lower alkoxy, amino, lower alkylamino, di-lower alkylamino, sulfo, sulfamoyl, iminomethyl, iminomethyl N-substituted by hydroxy, lower alkoxy, lower alkanoyloxy, lower alkyl or phenyl; or $R_1$ may be hydroxymethyl, halogen, hydroxy, formyl, carboxy, lower alkoxycarbonyl, carbamoyl, lower alkylcarbamoyl, di-lower alkylcarbamoyl or cyano; and $R_2$ is hydrogen, lower alkyl, lower alkoxy or halogen; and compounds of the formula I*, wherein n denotes 1, 2 or 3; $R_1$ is as defined above for compounds of formula I and $R_2$ represents hydrogen, lower alkyl, phenyl-lower alkyl, carboxy-lower alkyl, lower alkoxycarbonyl-lower alkyl, halogen, lower alkoxy, lower alkylthio, phenyl-lower alkylthio, phenylthio, carboxy, lower alkoxycarbonyl or lower alkanoyl; in a compound of formula I*, it being possible for the two substituents $C_6H_4$-$R_1$ and $R_2$ to be attached to any of the saturated carbon atoms of the saturated ring, either both to the same carbon atom or to different carbon atoms; stereoisomers, mixtures of these stereoisomers; and pharmaceutically acceptable salts thereof.

The invention relates more especially to compounds of formula I*, wherein n denotes 1, 2 or 3; $R_1$ represents lower alkyl, amino, lower alkylamino, di-lower alkylamino, hydroxymethyl, halogen, formyl, carboxy, lower alkoxycarbonyl, carbamoyl, lower alkylcarbamoyl, di-lower alkylcarbamoyl or cyano; and $R_2$ is hydrogen, lower alkyl, phenyl-lower alkyl, carboxy-lower alkyl, lower alkoxycarbonyl-lower alkyl, lower alkylthio, carboxy or lower alkoxycarbonyl; it being possible for the two substituents $C_6H_4$-$R_1$ and $R_2$ to be attached to any of the saturated carbon atoms of the saturated ring, either both to the same carbon atom or to different carbon atoms; to stereoisomers, mixtures of these stereoisomers; and pharmaceutically acceptable salts thereof.

Particular embodiments of the invention relate to the herein cited compounds of formula I, and compounds of the formula I* wherein n=1, 2 or 3, respectively.

Generally preferred are the compounds of the invention, wherein the substituents $C_6H_4$-$R_1$ is attached to the 5- or 7-position of the bicyclic ring system, and of particular importance are those compounds, wherein $C_6H_4$-$R_1$ is attached to the 5-position. In compounds of the invention, the substituent $R_1$ is preferably attached to the para- or meta-position, especially to the para-position, of the phenyl ring. The integer n in a compound of formula I* is preferably 1, 2 or 3, especially 1 or 2 and in particular 2. Most preferred are the compounds of formula I*.

A particular embodiment of the invention relates to the compounds of formula I* wherein n represents 2; $R_1$ represents hydrogen, lower alkyl, hydroxy-$C_2$–$C_7$-alkyl; lower alkyl substituted by amino, di-lower alkylamino, by 2 to 5 fluorine atoms, by carboxy, lower alkoxycarbonyl, carbamoyl, or cyano; nitro, lower alkoxy, amino, lower alkylamino, di-lower alkylamino, sulfo, sulfamoyl, iminomethyl, iminomethyl N-substituted by hydroxy, lower alkoxy, lower alkanoyloxy, lower alkyl or phenyl; and $R_2$ represents hydrogen; and pharmaceutically acceptable salts thereof.

Another particular embodiment of the invention relates to the compounds of formula I* wherein n represents 2; $R_1$ represents hydroxymethyl, halogen, formyl, carboxy, lower alkoxycarbonyl, carbamoyl, lower alkylcarbamoyl, di-lower alkylcarbamoyl or cyano; and $R_2$ represents hydrogen; and pharmaceutically acceptable salts thereof.

A further particular embodiment of the invention relates to the compounds of formula I* wherein n represents 2; $R_1$ represents hydroxymethyl, halogen, hydroxy, formyl, carboxy, lower alkoxycarbonyl, carbamoyl, lower alkylcarbamoyl, di-lower alkylcarbamoyl or cyano; and $R_2$ represents lower alkyl, phenyl-lower alkyl, carboxy-lower alkyl, lower alkoxy-carbonyl-lower alkyl, lower alkylthio, carboxy or lower alkoxycarbonyl; it being possible for the two substituents $C_6H_4$-$R_1$ and $R_2$ to be attached to any of the saturated carbon atoms of the saturated ring, either both to the same carbon atoms or to different carbon atoms; to stereoisomers, mixtures of these stereoisomers; and pharmaceutically acceptable salts thereof.

A preferred embodiment of the invention relates to the compounds of formula I wherein $R_1$ represents cyano or halogen, especially cyano; and $R_2$ is hydrogen, lower alkyl, lower alkoxy or halogen, especially hydrogen; and pharmaceutically acceptable salts thereof.

A further preferred embodiment of the invention relates to the compounds of formula I* wherein n represents 1, 2 or 3, especially 1 or 2; and in particular 2; $R_1$ represents cyano or halogen, especially cyano; and $R_2$ is hydrogen, lower alkyl, phenyl-lower alkyl, carboxy-lower alkyl, lower alkoxycarbonyl-lower alkyl, lower alkylthio, carboxy or lower alkoxycarbonyl, especially hydrogen; the two substituents $C_6H_4$-$R_1$ and $R_2$ to be attached to any of the saturated carbon atoms of the saturated ring, either both to the same carbon atom or to different carbon atoms; stereoisomers, mixtures of these stereoisomers and pharmaceutically acceptable salts thereof.

Further preferred are the said compounds of formula I* wherein the substituents $C_6H_4$-$R_1$ and $R_2$ are both attached at the 5-position of the bicyclic ring system; and $R_1$ represents para-cyano.

A further particular embodiment of the invention are the compounds of formula Ia

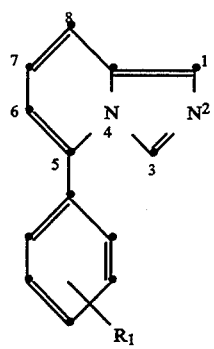

(Ia)

wherein $R_1$ represents cyano, nitro or $C_1$-$C_4$-alkyl, the 7,8-dihydro derivatives thereof and the 5,6,7,8-tetrahydro derivatives thereof of the formula Ib

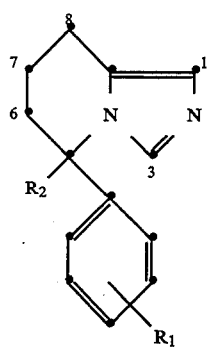

(Ib)

wherein $R_1$ is as defined under formula Ia and $R_2$ is hydrogen, $C_1$-$C_4$-alkyl, aryl-$C_1$-$C_4$-alkyl, halogen, etherified or esterified hydroxy, etherified or esterified mercapto, carboxy-$C_1$-$C_4$-alkyl, $C_1$-$C_4$-alkoxycarbonyl-$C_1$-$C_4$-alkyl or $C_1$-$C_4$-alkanoyl, stereoisomers, mixtures of these stereoisomers and salts of these compounds.

The 5,6,7,8-tetrahydro-derivatives of the formula Ib have a chiral C-atom in the 5-position. The 5R- and the 5S-enantiomers as well as the 5(R,S)-racemate fall within the scope of the present invention.

The generic terms used for the compounds of formula Ia and Ib preferably are defined as follows:

$C_1$-$C_4$-Alkyl $R_1$ or $R_2$ is, for example, ethyl, n-propyl, isopropyl, n-butyl, sec-butyl, or tert-butyl and preferably methyl.

Halogen $R_2$ is, for example, fluoro or bromo or, preferably, chloro.

Aryl-$C_1$-$C_4$-alkyl $R_2$ is, for example, benzyl.

Etherified hydroxy or mecapto $R_2$ is, for example, a hydroxy or mercapto group which is etherified by $C_1$-$C_4$-alkyl, for example methyl or ethyl, aryl-$C_1$-$C_4$-alkyl, for example benzyl, 2-phenylethyl or diphenylmethyl, or aryl, for example phenyl.

Etherified hydroxy or mercapto $R_2$ is, preferably, $C_1$-$C_4$-alkoxy, for example methoxy or ethoxy, $C_1$-$C_4$-alkylthio, for example methyl- or ethylthio, aryl-$C_1$-$C_4$-alkylthio, for example benzylthio, 2-phenylethylthio or diphenylmethylthio, or is arylthio, for example phenylthio.

Esterified hydroxy or mercapto $R_2$ is, for example, a hydroxy or mercapto group which is esterified by acyl, for example $C_1$-$C_4$-alkanoyl, for example, formyl or acetyl.

Carboxy-$C_1$-$C_4$-alkyl $R_2$ is, for example, carboxymethyl or 2-carboxyethyl.

$C_1$-$C_4$-Alkoxycarbonyl-$C_1$-$C_4$-alkyl $R_2$ is, for example, methoxy- or ethoxycarbonylmethyl.

$C_1$-$C_4$-Alkanoyl $R_2$ is, for example, formyl, acetyl or propionyl.

The invention especially relates to said compounds of the formula Ia, wherein $R_1$ represents cyano, and the 7,8-dihydro derivatives thereof, and the 5,6,7,8-tetrahydro derivatives thereof of the formula Ib, wherein $R_1$ is cyano and $R_2$ is hydrogen, $C_1$-$C_4$-alkyl, for example methyl or ethyl, $C_1$-$C_4$-alkoxy, for example methoxy or ethoxy, $C_1$-$C_4$-alkylthio, for example methyl- or ethylthio, aryl-$C_1$-$C_4$-alkylthio, for example benzylthio, 2-phenylethylthio or diphenylmethylthio, arylthio, for example phenylthio, or $C_1$-$C_4$-alkanoyl, for example formyl or acetyl, and pharmaceutically acceptable acid addition salts of a compound of the formula Ia or Ib.

Particularly preferred are said compounds of formula Ia, wherein $R_1$ is cyano, advantageously attached to the para-position, the 7,8-dihydro derivatives thereof and the 5,6,7,8-tetrahydro derivatives thereof of the formula Ib, wherein $R_1$ is as defined for formula Ia and $R_2$ is hydrogen, and pharmaceutically acceptable acid addition salts thereof.

The invention preferably relates to compounds of the formula Ic

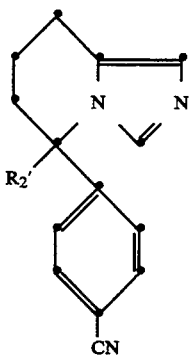

(Ic)

wherein $R_2'$ is hydrogen, $C_1$–$C_4$-alkyl, for example methyl or ethyl, $C_1$–$C_4$-alkoxy, for example methoxy or ethoxy, $C_1$–$C_4$-alkylthio, for example methyl- or ethylthio, aryl-$C_1$–$C_4$-alkylthio, for example benzylthio, 2-phenylethylthio or diphenylmethylthio, arylthio, for example phenylthio, or $C_1$–$C_4$-alkanoyl, for example formyl or acetyl, and pharmaceutically acceptable acid addition salts thereof.

Most preferred is the compound of the formula Ic, wherein $R_2'$ is hydrogen, and pharmaceutically acceptable acid addition salts of this compound.

Also preferred are the compounds of formula Ia, wherein $R_1$ represents hydrogen, esterified hydroxy, especially halogen or a sulfonyloxy group, such as p-toluenesulfonyloxy, benzenesulfonyloxy or mesyloxy; sulfo, amino, carbamoyl, lower alkylcarbamoyl, e.g. tert-butylcarbamoyl, or a formyl group in the form of a functional derivative, e.g. hdyroxyiminomethyl; and the 5,6,7,8-tetrahydro compounds of formula Ib, wherein $R_1$ is as defined above for formula Ia and $R_2$ is hydrogen, $C_1$–$C_4$-alkyl, aryl-$C_1$–$C_4$-alkyl, such as benzyl; halogen, etherified hydroxy, such as $C_1$–$C_4$-alkoxy; esterified hydroxy, such as acyloxy, e.g. $C_1$–$C_4$-alkanoyloxy; etherified mercapto, such as $C_1$–$C_4$-alkylthio, aryl-$C_1$–$C_4$-alkylthio, e.g. benzylthio, 2-phenylethylthio or diphenylmethylthio, or arylthio, e.g. phenylthio; esterified mercapto, such as acylthio, e.g. $C_1$–$C_4$-alkanoylthio; carboxy-$C_1$–$C_4$-alkyl, $C_1$–$C_4$-alkoxycarbonyl-$C_1$–$C_4$-alkyl or $C_1$–$C_4$-alkanoyl; and pharmaceutically acceptable salts thereof.

Of said compounds of formulae Ia and Ib are those of special interest, wherein $R_1$ represents halogen or carbamoyl, and in particular bromo.

Another preferred embodiment of the invention are compounds of formula Ia, wherein $R_1$ is hydrogen, esterified hydroxy, especially a sulfonyloxy group, such as p-toluenesulfonyloxy, benzenesulfonyloxy or mesyloxy; sulfo, amino or formyl in the form of a functional derivative, such as hydroxyiminomethyl; and the 5,6,7,8-tetrahydro compounds of formula Ib, wherein $R_1$ is as defined above for formula Ia and $R_2$ is hydrogen; or wherein $R_1$ represents hydrogen, esterified hydroxy, especially halogen or a sulfonyloxy group, such as p-toluenesulfonyloxy, benzenesulfonyloxy or mesyloxy; sulfo, amino, carboxy, carboxy in the form of a functional derivative, such as carbamoyl, lower alkylcarbamoyl, e.g. tert-butylcarbamoyl, formyl or a formyl group in the form of a functional derivative, e.g. hydroxyiminomethyl, and $R_2$ is $C_1$–$C_4$-alkyl, aryl-$C_1$–$C_4$-alkyl, halogen, etherified or esterified hydroxy, etherified or esterified mercapto, carboxy-$C_1$–$C_4$-alkyl, $C_1$–$C_4$-alkoxycarbonyl-$C_1$–$C_4$-alkyl or $C_1$–$C_4$-alkanoyl; and pharmaceutically acceptable salts thereof.

A further particular embodiment of the invention relates to the compounds of formula Id

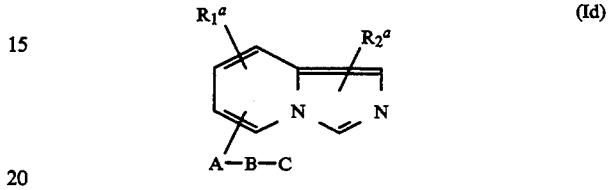

(Id)

and 5,6,7,8-tetrahydro derivatives thereof, wherein $R_1^a$ is hydrogen, halogen, lower alkyl, lower alkoxy, hydroxy or aryl-lower alkoxy in which aryl represents phenyl or phenyl substituted by lower alkoxy, lower alkyl, halogen or trifluoromethyl; $R_2^a$ represents hydrogen; C represents carboxy, lower alkoxycarbonyl, unsubstituted or mono- or di-(lower alkyl)-substituted carbamoyl, cyano, formyl, hydroxymethyl, 5-tetrazolyl, 4,5-dihydro-2-oxazolyl, 4,5-dihydro-2-oxazolyl substituted by lower alkyl, or hydroxycarbamoyl; A represents a direct bond; B represents phenylene; and pharmaceutically acceptable salts thereof.

A more particular embodiment thereof relates to the compounds of formula Id and 5,6,7,8-tetrahydro derivatives thereof wherein A represents a direct bond; B represents phenylene; C represents carboxy, lower alkoxycarbonyl, carbamoyl, hydroxycarbamoyl, 5-tetrazolyl or hydroxymethyl; $R_1^a$ and $R_2^a$ are hydrogen; and pharmaceutically acceptable salts thereof.

Preferred are the said compounds of formula Id and 5,6,7,8-tetrahydro derivatives thereof wherein the group B-C is directly attached at the 5-position of the imidazo [1,5-a]pyridine nucleus.

A particular embodiment thereof relates to the compounds of formula Ie

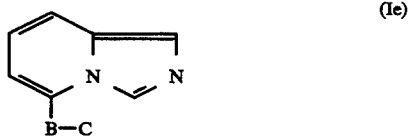

(Ie)

wherein B represents phenylene; C represents carboxy, lower alkoxycarbonyl or carbamoyl; and pharmaceutically acceptable salts thereof.

A further embodiment relates to the 5,6,7,8-tetrahydro derivatives thereof.

The compounds of the instant invention have valuable pharmacological properties. For example, they are useful as inhibitors of aromatase activity in mammals, and for treating conditions responsive thereto. For example, these compounds inhibit the metabolic conversion of androgens to estrogens. Thus, the compounds of formula I and I* are useful e.g. in the treatment of gynecomastia, i.e. male breast development, by inhibiting the aromatization of steroids in males susceptible to this condition. Moreover, the compounds of formula I and I* are useful e.g. in the treatment of estrogen dependent diseases, for example estrogen dependent female breast cancer, especially in postmenopausal females, by inhibiting estrogen biosynthesis. These effects are demonstrable in in vitro assay tests or in vivo animal tests using advantageously mammals, e.g. guinea pigs, mice, rats, cats, dogs, or monkeys. The applied dosage may range between about 0.01 and 50 mg/Kg, preferably between about 0.01 to 10 mg/Kg.

The in vitro inhibition of aromatase activity of the compounds of the present invention can be demonstrated as follows:

A microsomal fraction is prepared from fresh term human placenta by the method described by Thompson and Siiteri, J. Biol. Chem., Vol. 249, p. 5364 (1974). The microsomal preparation so obtained is lyophilized and stored at $-40°$ C. in a dessicator.

The assay is performed in a total volume of 1 ml of 0.05M potassium phosphate buffer (pH 7,4) at 37° C. The incubation mixture contains $1.135 \times 10^{-7}$M [4-$^{14}$C]-androstene-3,17-dione (New England Nuclear, SA 59.7 mCi/mmole), $2.4 \times 10^{-4}$M NADPH (Sigma, tetrasodium salt Type III), varying concentrations of the test compound and 226 g/ml of the microsomal enzyme preparation, which is equivalent to 120 µg of microsomal protein as determined by the method of Lowry et. al., J. Biol. Chem., Vol. 193, p, 265 (1951). After 20 minutes of incubation the mixture is extracted twice with 7 volumes of ethyl acetate, and the combined extracts are evaporated to dryness. The resulting residue is separated by chromatography for 65 minutes on thin-layer plates precoated with silica gel 60 using a mixture of ethyl acetate with isooctane (70:30 v/v) as solvent system. The radioactive zones of the plate are located, and the estrone peak is identified by comparison with an authentic standard. The corresponding band of silica gel is transferred to counting vials for detection with a liquid scintillation detector. Neither the substrate concentration nor the NADPH is rate limiting in this system. The number of counts emitted from estrone is calculated in the absence of the test compound and for each concentration of the test compound. The $IC_{50}$ values are determined graphically as the concentration of the test compound as which the counted pertaining to the amount of estrone formed is reduced to 50% of the control value. $IC_{50}$ values range from about $10^{-6}$ to about $10^{-9}$ M.

With 5-p-cyanophenyl-5,6,7,8-tetrahydroimidazo-[1,5-a]pyridine as representative test compound, an $IC_{50}$ of $4.5 \times 10^{-9}$ M is obtained according to the method mentioned above.

The in vivo inhibition of aromatase activity of the compounds of the present invention can be demonstrated as follows:

Twenty-one-day-old female rats are injected subcutaneously with 10 IU pregnant mare serum gonadotropin (PMS). Two days later the same rats are injected subcutaneously with 30 IU human chorionic gonadrotropin (hCG). On the day following the hCG treatment the rates are injected subcutaneously with either propylene glycol (0.2 ml:p.o.) or with various doses of the test compound. One hour later all of the rats are treated with 2.25 mg 4-androstene-3,17-dione in 0.1 ml oil, subcutaneously. Four hours after the injection of androstenedione the rats are killed and their ovaries removed and trimmed free of adhering tissue and stored in pairs at $-40°$ C. To determine the total estrogen content of the ovaries, 1.5 ml of 0.05M aqueous potassium phosphate buffer, pH 7.4, and 0.2 ml of 0.1N aqueous sodium hydroxide are added to the tissues which are then homogenized. The homogenate is extracted with 15 ml of diethyl ether, 5 ml aliquots are radioimmunoassayed with antiserum having 100% cross reactivity with estrone, estradiol and estriol. The results are expressed as ng estrogen/pair of ovaries.

When 5-p-cyanophenyl-5,6,7,8-tetrahydroimidazo[1,5-a]pyridine is tested as a representative compound for in vivo inhibition of aromatase activity according to the in vivo test described, supra, a statistically significant inhibition of estrogen synthesis is obtained at doses of 0.1, 0.05, and 0.025 moles/100 g ($P<0.05$) as shown in the following Table:

TABLE

Suppression of Ovarian Estrogen Content of PMS-hCG Primed Rats by 5-p-cyanophenyl-5,6,7,8-tetrahydroimidazo[1,5-a]-pyridine Given 1 Hour Prior to Androstenedione (n = 6/group)

| Dose µmoles/100 g | Mean Ovarian Estrogen Content ng/pair of Ovaries + S.E. |
|---|---|
| 0 | $1.187 \pm 0.044$ |
| 0.1 | $0.072 \pm 0.003$ |
| 0.05 | $0.153 \pm 0.013$ |
| 0.025 | $0.194 \pm 0.031$ |

Illustrative of the invention, minimal effective doses in vivo for aromatase inhibition (suppression of ovarian estrogen content of female rats) are:

| Compound of example | Minimal effective dose (mg/kg p.o.) |
|---|---|
| 1 | 0.0026 |
| 3 | 0.013 |
| 17 | 0.133 |
| 31 | 0.025 |
| 32 | 0.411 |
| 33 | 0.346 |

The antitumor activity, especially in estrogen-dependent tumors, can be demonstrated in vivo e.g. in dimethylbenzanthracene (DMBA)-induced mammary tumors in female Sprague-Dawley rats [see Proc. Soc. Exp. Biol. Med. 160, 296–301 (1979)]. Compounds of the invention cause regression of existing tumors and suppress the appearance of new tumors at daily doses of about 1 to about 20 mg/kg p.o. or less. Illustrative of the invention, 5-p-cyanophenyl-5,6,7,8-tetrahydroimidazo[1,5-a]pyridine is effective at a daily dose of about 0.1 mg/Kg p.o. administered to rats.

Surprisingly, while the compounds of the invention are found to be effective aromatase inhibitors in vitro and in vivo, they apparently are devoid of cholesterol side-chain cleavage inhibitory activity in vivo, since they do not induce adrenal hypertrophy as verified by endocrine organ evaluation.

Due to their pharmacological properties as aromatase inhibitors, the compounds of the invention can be used as medicaments, for example in the form of pharmaceutical compositions, for the treatment of conditions responsive to aromatase inhibition, such as hormonal diseases, e.g. estrogen dependent tumours, especially mammary carcinoma, and anomalies, e.g. gynecomastia, in mammals, including man.

Compounds of the invention also demonstrate activity as thromboxane synthetase inhibitors. These are thus also useful for treating conditions responsive to thromboxane synthetase inhibition in mammals, e.g. for the treatment of cardiovascular disease such as thrombosis and thromboembolisms.

Thromboxane synthetase inhibition is demonstrated in vitro or in vivo using advantageously mammals, e.g. guinea pigs, mice, rats, cats, dogs, or monkeys. Said compounds can be administered to them enterally or parenterally, advantageously orally, or subcutaneously, intravenously or intraperitoneally, for example, within gelatin capsules, or in the form of starchy suspensions or aqueous solutions respectively. The applied dosage may range between about 1.0 and 50 mg/kg/day.

The in vitro inhibition of the thromboxane synthetase enzyme can be demonstrated, analogous to the method of Sun, Biochem. Biophys. Res. Comm. 74, 1432 (1977); the testing procedure is as follows:

$^{14}$C-arachidonic acid is incubated with an enzyme preparation consisting of solubilized and partially purified prostaglandin cyclo-oxygenase from sheep seminal vesicles and a crude microsomal preparation of thromboxane synthetase from lysed hyman platelets. The test compound (dissolved in buffer, or if necessary, in a small amount of ethanol) is added to the incubation medium. At the end of the incubation period (30 minutes), Prostaglandin $E_2$ (PGE$_2$) is reduced to a mixture of Prostaglandin F$_2\alpha$ and F$_2\beta$ (PGF$_2\alpha+\beta$) by addition of sodium borohydride. The radioactive products and excess substrate are extracted into ethyl acetate; the extract is evaporated to dryness; the residue is dissolved in acetone, spotted on thin-layer plates and chromatographed in the solvent system toluene: acetone: glacial acetic acid (100 volumes:100volumes:3 volumes). The radioactive zones are located; those corresponding to Thromboxane B$_2$ (TxB$_2$) and PGF$_2$ $\alpha+\beta$ are transferred to liquid scintillation vials and counted. The ratio of counts for TxB$_2$/PGF$_2$ $\alpha+\beta$ is calculated for each concentration of test compound and IC$_{50}$ values are determined graphically as the concentration of test compound at which the ratio of TxB$_2$/PGF$_2$ $\alpha+\beta$ is reduced to 50% of the control value.

The inhibition of the synthesis and the reduction of plasma levels of thromboxane is determined in vivo on administration to rats in the following manner (as adapted from the procedures described by Tai et al. in Anal. Biochem. 87:343, 1978 and by Salmon in Prostaglandins 15:383, 1978):

Rats are dosed with vehicle or test drug and injected intravenously with ionophore A23187 (0.5 mg/kg) two hours later. Blood is collected for analysis 2 minutes after the ionophore injection. A single aliquot of each plasma sample is assayed for thromboxane B$_2$ and another aliquot for 6-keto-PGF$_{1\alpha}$, the stable metabolites of thromboxane A$_2$ and prostacyclin (PGI$_2$) respectively, by radioimmunoassay.

Illustrative of thromboxane synthetase inhibitory activity, 5-(p-carboxyphenyl)-5,6,7,8-tetrahydroimidazo[1,5-a]pyridine has an IC$_{50}$ of about $9\times10^{-7}$M for thromboxane synthetase inhibition in vitro.

Particularly preferred as thromboxane synthetase inhibitors are the compounds of the invention wherein R$_1$ represents carboxy or functionally modified carboxy.

Particularly preferred as aromatase inhibitors are the compounds of the invention wherein R$_1$ represents cyano or halogen.

Compounds of formula I or I*, comprising the compounds of formula Ia and Ib, are prepared by processes known per se, preferably by a) cyclising a compound of formula II

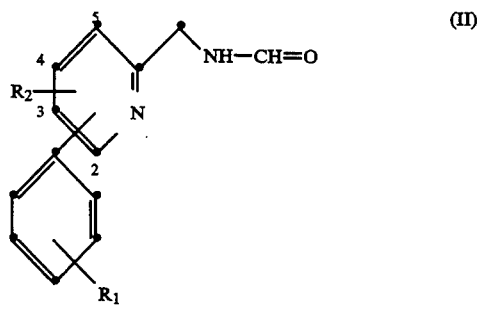

or the 4,5-dihydro derivatives thereof, in order to obtain a compound of formula I or a 7,8-dihydro derivative thereof respectively, or b) cyclising a compound of formula III

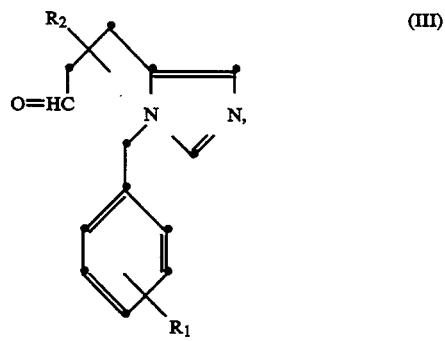

wherein R$_2$ may be attached to any of the carbon atoms indicated inclusive the carbonyl carbon, in order to obtain a 7,8-dihydro derivative of a compound of formula I wherein the substituent C$_6$H$_4$-R$_1$ is attached to the 5-position, or c)/f) converting in a compound of formula IV or VII

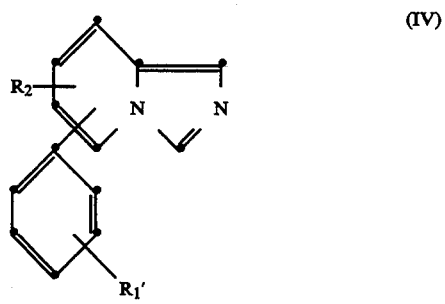

-continued

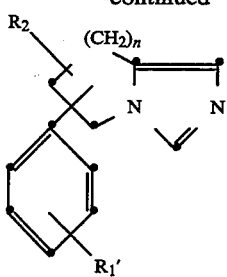

or in a 7,8-dihydro derivative of formula IV, wherein $R_1'$ is a group that can be converted to the cyano group, $R_1'$ to cyano, in order to obtain a compound of formula I, a 7,8-dihydro derivative thereof, or a compound of formula I* respectively, wherein $R_1$ represents cyano, or d) cyclising a compound of formula V

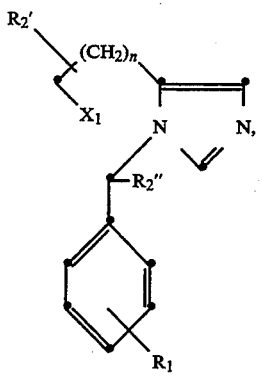

wherein at least one of the radicals $R_2'$ and $R_2''$ is hydrogen and the other represents a radical $R_2$ as defined under formula I*, and $X_1$ is a leaving group, and $R_2'$ may be attached to any of the carbon atoms indicated, in order to obtain a compound of formula I*, wherein the substituent $C_6H_4$-$R_1$ is attached to the 5-position; or $X_1$ represents =CH—COOH or a lower alkylester thereof, $R_2'$ is hydrogen and $R_2''$ is as defined under formula I*, in order to obtain a compound of formula I*, wherein the substituent $C_6H_4$-$R_1$ is attached to the 5-position and the 6-position is substituted by carboxymethyl or lower alkoxycarbonylmethyl, or e) cyclising a compound of formula VI

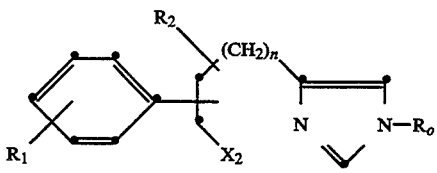

wherein the substituents $C_6H_4$-$R_1$ and $R_2$ may be attached to any of the carbon atoms indicated, either both radicals to the same carbon atom or to different carbon atoms, $R_o$ is a NH protecting group or hydrogen, and $X_2$ is a leaving group, in order to obtain a compound of formula I*; or g) cyclising a compound of formula IX

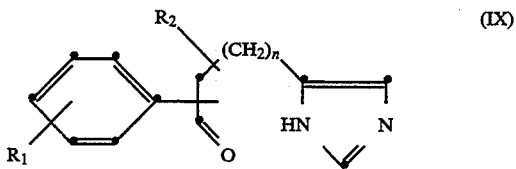

wherein the substituents $C_6H_4$-$R_1$ and $R_2$ may be attached to any of the carbon atoms indicated inclusive the carbonyl carbon, either both radicals to the same carbon atom or to different carbon atoms, optionally under reductive conditions, in order to obtain a 7,8-dihydro derivative of a compound of formula I or, in case of reductive conditions, a compound of formula I*, or h) decarboxylating a compound analogous to formula I, or a 7,8-dihydro derivative thereof, or a compound analogous to formula I*, each of which containing an additional carboxy group in 1- or 3-position, in order to obtain a compound of formula I, a 7,8-dihydro derivative thereof, or a compound of formula I* respectively; wherein in the above starting materials of the formulae II to VII and IX the symbols n, $R_1$ and $R_2$ have the meanings given under formulae I and I* respectively; and/or, if desired, reducing a compound of formula I, or a 7,8-dihydro derivative thereof to the corresponding 5,6,7,8-tetrahydro derivative of formula I* optionally with simultaneous reduction of the substituent(s) $R_1$ and/or $R_2$ into (an)other group(s) $R_1$ and/or $R_2$; and/or, if desired, decarboxylating a compound of formula I*, wherein $R_2$ is carboxy, in order to obtain a compound of formula I* wherein $R_2$ is hydrogen; and/or, if desired, converting a compound obtained into another compound of the invention and/or converting a salt obtained into the free compound or into another salt and/or converting a free compound into a salt and/or separating a mixture of isomers or racemates obtained into the single isomers or racemates and/or resolving an enantiomeric mixture, such as a racemate, into the optical isomers.

The compounds of the formulae Ia or Ib are prepared by the following process preferably by a) cyclizing a compound of the formula IIa

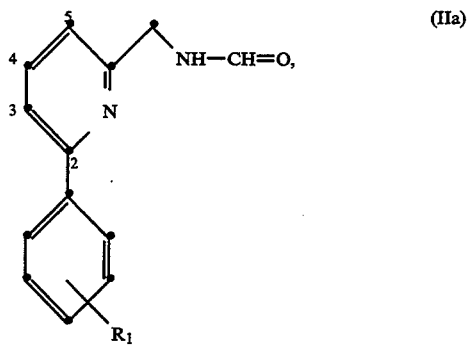

wherein $R_1$ is as defined above under formula Ia, or the 4,5-dihydro derivative thereof, under acidic conditions, in order to obtain a compound of formula Ia or a 7,8-dihydro derivative thereof, or b) for the preparing of the 7,8-dihydro derivative of a compound of formula Ia, cyclizing a compound of the formula IIIa

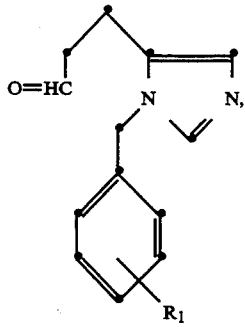

(IIIa)

wherein $R_1$ is as defined above under formula Ia, under basic conditions, or c) converting in a compound of the formula IVa

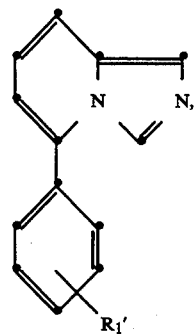

(IVa)

wherein $R_1'$ is a group or radical that can be converted to the cyano group, or in the 7,8-dihydro derivative thereof, $R_1'$ to cyano, in order to obtain a compound of formula Ia, or d) cyclizing a compound of the formula Vb

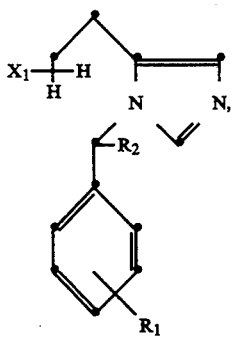

(Vb)

wherein $R_1$ and $R_2$ are as defined above under formula Ib and $X_1$ is a leaving group, in the presence of a base, in order to obtain a compound of formula Ib, or e) cyclizing a compound of the formula VIb

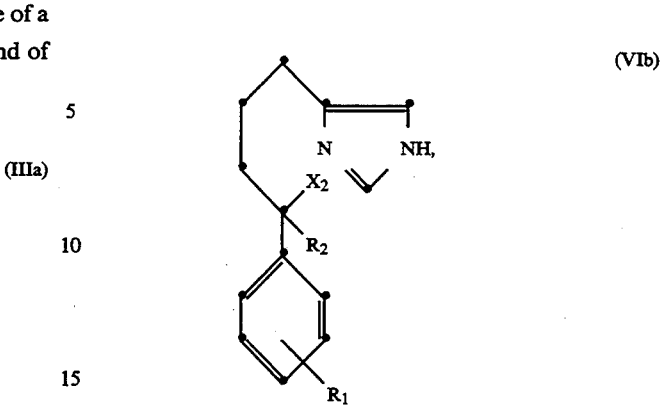

(VIb)

wherein $R_1$ and $R_2$ are as defined above under formula Ib and $X_2$ is a leaving group, in the presence of a base, in order to obtain a compound of formula Ib, or f) converting in a compound of the formula VIIb

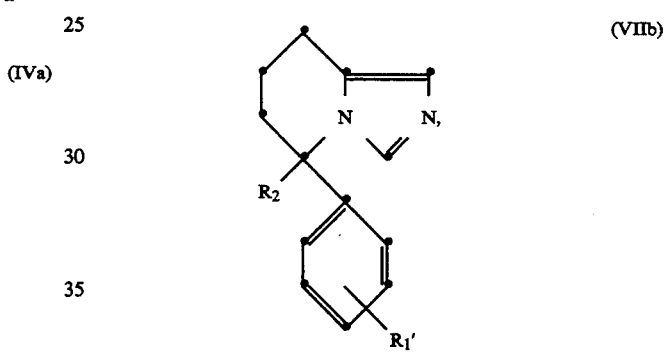

(VIIb)

wherein $R_1'$ is a group or radical that can be converted to the cyano group, and wherein $R_2$ is as defined above under formula Ib, the group $R_1'$ to cyano, in order to obtain a compound of formula Ib, wherein $R_1$ is cyano; and/or, if desired, reducing a compound of the formula Ia, or the 7,8-dihydro derivative thereof with hydrogen in the presence of a hydrogenation catalyst to the corresponding 5,6,7,8-tetrahydro derivative of the formula Ib, and/or, if desired, converting a compound obtained into another compound of the invention and/or converting a salt obtained into the free compound or into another salt and/or converting a free compound having a salt-forming group into a salt and/or separating a racemic mixture obtained into the individual enantiomers.

Further processes for the preparation of compounds of the formulae Ia or Ib are e.g.

a modification of process e) wherein compounds of formula VIb are used wherein the free NH group is protected by a NH protecting group as defined below, or g) cyclising a compound of formula IXb

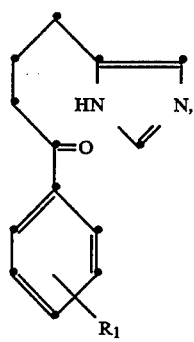
(IXb)

optionally under reductive conditions, in order to obtain a 7,8-dihydro derivative of a compound of formula Ia or, in case of reductive conditions, a compound of formula Ib, or h) decarboxylating a compound analogous to formula Ia, or a 7,8-dihydro derivative thereof, or a compound analogous to formula Ib, each of which containing an additional carboxy group in 1- or 3-position, in order to obtain a compound of formula Ia, a 7,8-dihydro derivative thereof, or a compound of formula Ib respectively.

Process a)

The cyclization of the formylamino compound of the formula II or IIa is advantageously carried out under conditions such as described for the cyclization of 6-methyl-2-methylaminopyridine to 5-methylimidazo[1,5-a]pyridine in J. Org. Chemistry 40, 1210 (1975). Said cyclization under acid conditions may be achieved advantageously with a Lewis acid, such as polyphosphoric acid, phosphorous oxychloride or polyphosphate ester.

Process b)

The cyclization of the formyl compound of the formula III or IIIa is carried out e.g. under basic conditions. The base employed in this process is any base that readily accepts protons, for example an amine, e.g. a tertiary amine such as a tri-lower alkylamine, e.g. trimethylamine or triethylamine, a cyclic tertiary amine such as N-methylmorpholine, a bicyclic amidine, e.g. a diazabicycloalkene, such as 1,5-diazabicyclo[4.3.0]non-5-ene or 1,5-diazabicyclo[5.4.0]undec-5-ene (DBU), or is, for example, a base of the pyridine type, e.g. pyridine. A suitable base is also an inorganic base, for example an alkali metal hydroxide or alkaline earth metal hydroxide, e.g. sodium, potassium or calcium hydroxide. A preferred base is an alcoholate, for example an alkali metal alcoholate, e.g. sodium or potassium methylate, ethylate or tertbutylate.

The cyclization according to processes a) and b) is generally carried out in organic inert solvents, such as suitable alcohols, such as methanol, ethanol or isopropanol, ketones, such as acetone, ethers, such as dioxan or tetrahydrofuran, nitriles, such as acetonitrile, hydrocarbons, such as benzene or toluene, halogenated hydrocarbons, such as methylene chloride, chloroform or carbon tetrachloride, esters, such as ethyl acetate, or amides, such as dimethylformamide or dimethylacetamide, and the like. The reaction temperature is between room temperature and the boiling temperature of the reaction mixture, preferably between 60° C. and the boiling temperature of the reaction mixture. Furthermore, the cyclization is preferably carried out under an inert gas atmosphere, especially a nitrogen atmosphere.

Process c)/f)

A group of radical $R_1'$ in a compound of the formula IV, IVa, VII or VIIb, which can be converted into the —CN group, is, for example, hydrogen, esterified hydroxy, for example halo, especially chloro, bromo, or iodo, or a sulfonyloxy group, for example p-toluenesulfonyloxy, benzenesulfonyloxy or mesyloxy, sulfo, amino, carboxy, carboxy in the form of a functional derivative, for example carbamoyl, lower alkylcarbamoyl, for example t-butylcarbamoyl, or haloformyl, for example chloro- or bromoformyl, formyl, a formyl group in the form of a functional derivative, for example hydroxyiminomethyl, or a halomagnesium group, for example iodo-, bromo- or chloromagnesium.

Compounds of the formula I, Ia, I* or Ib, wherein $R_1$ is cyano, can be obtained, for example, by carrying out the following conversions:

The conversion of a compound of the formula IV, IVa, VII or VIIb wherein $R_1'$ is hydrogen, to a compound of the formula I, Ia, I* or Ib is performed e.g. according to the known method of C. Friedel, F. M. Crafts and P. Karrer by reacting with cyanogen chloride (ClCN) of bromide or according to the method of J. Houben and W. Fisher, by reacting with e.g. trichloroacetaonitrile. Advantageously, the standard catalyst aluminium chloride is used in these reactions and hydrogen chloride or hydrogen bromide is split off, which can be removed from the reaction mixture after addition of a base, preferably an amine, for example triethylamine or pyridine.

The conversion of a compound of the formula IV, IVa, VII or VIIb, wherein $R_1'$ is halo, for example chloro, bromo or iodo, to a compound of the formula I, Ia, I* or Ib is performed by using e.g. a cyanide salt, especially sodium or potassium cyanide or, preferably, copper(I) cyanide. Preferred solvents for this reaction are pyridine, quinoline, dimethylformamide, 1-methyl-2-pyrrolidinone and hexamethylphosphoric triamide. High temperatures, especially reflux temperatures of the reaction mixture are preferred.

The conversion of a compound of the formula IV, IVa, VII or VIIb, wherein $R_1'$ is a sulfonyloxy group, for example p-toluenesulfonyloxy, benzenesulfonyloxy or mesyloxy, to a compound of the formula I, Ia, I* or Ib is performed e.g. by reaction with an alkali metal cyanide, preferably sodium or potassium cyanide. High temperatures, especially the reflux temperature of the reaction mixture, are preferred.

The conversion of a compound of the formula IV, IVa, VII or VIIb, wherein $R_1'$ is amino, to a compound of the formula I, Ia, I* or Ib proceeds over several steps. Firstly, a diazonium salt is formed e.g. by reaction of the amino compound with an alkali nitrite salt, preferably potassium nitrite. The diazonium salt can be reacted according to the known reaction named after Sandmeyer in situ e.g. with cuprous cyanide or a cyanide complex with labile cyano groups, preferably potassium cuproammonium cyanide, or with catalytic amounts of freshly precipitated copper powder in the presence of an alkali metal cyanide, for example sodium or potassium cyanide. This reaction is referenced in detail e.g. in Houben-Weyl, Methoden der Organsichen Chemie, Thiene Stuttgart 1952, Vol. VIII.

A carboxy group $R_1'$ can be converted to cyano e.g. by reaction with chlorosulfonylisocyanate according to the method of R. Graf, Angew. Chem. 80, 183 (1968). Dimethylformamide is the preferred solvent, carbon dioxide is evolved and the chlorosulfonic acid-dimethylformamide addition salt is precipitated in this reaction.

The conversion of a compound of the formula IV, IVa, VII or VIIb, wherein $R_1'$ is a carboxy group in the form of a functional derivative, for example carbamoyl, lower alkylcarbamoyl, for example t-butylcarbamoyl, to a compound of the formula I, Ia, I* or Ib is performed e.g. with a strong dehydrating agent, such as phosphorus pentoxide, phosphoryl chloride, thionyl chloride, phosgene or oxalyl chloride.

A haloformyl (=halocarbonyl) group $R_1'$, for example chloro- or bromoformyl, is reacted with ammonia or a primary or secondary amine, for example methyl- or dimethylamine. The amide thus obtained is converted to the nitrile of the formula I, Ia, I* or Ib, optionally in situ, with the dehydrating agents mentioned above, for example phosphorous pentachloride in case of the unsubstituted amide or phosphoryl chloride in case of a mono- or di-lower alkylated amide.

The dehydration can be preferably carried out in the presence of a suitable base. A suitable base is, for example, an amine, for example a tertiary amine, for example tri-lower alkylamine, for example trimethylamine, triethylamine or ethyl diisopropylamine, or N,N-di-lower alkylaniline, for example N,N-dimethylaniline, or a cyclic tertiary amine, for example a N-lower alkylated morpholine, for example N-methylmorpholine, or is, for example, a base of the pyridine type, for example pyridine or quinoline.

The conversion of a formyl group to a cyano group is carried out e.g. by converting the formyl group to a reactive functional derivative, for example a hydroxyiminomethyl group, and converting this group to cyano by a dehydrating agent. A suitable dehydrating agent is one of the inorganic dehydrating agents mentioned above, for example phosphorous pentachloride, or, preferably, the anhydride of an organic acid, for example the anhydride of a lower alkane carboxylic acid, for example acetic acid anhydride.

The conversion of the formyl group to hydroxyiminomethyl is carried out by reacting a compound of formula IV, IVa, VII or VIIb, wherein $R_1'$ is formyl, e.g. with an acid addition salt of hydroxylamine, preferably the hydrochloride.

A compound of the formula IV, IVa, VII or VIIb, wherein $R_1'$ is formyl, can be converted directly to a compound of the formula I, Ia, I* or Ib, e.g. by reaction with O,N-bis-(trifluoroacetyl)hydroxylamine in the presence of a base, for example pyridine, according to the method of D. T. Mowry, Chem. Rev. 42, 251 (1948).

The conversion of a compound of the formula IV, IVa, VII or VIIb, wherein $R_1'0$ is a halomagnesium group, for example, iodo-, bromo-, or chloromagnesium, to a compound of the formula I, Ia, I* or Ib, is performed e.g. by reacting the magnesium halide with cyanogen halide or dicyanogen. Magnesium halide, for example magnesium chloride, or magnesium cyanohalide, for example magnesium cyanochloride, is produced during this reaction. The "Grignard" compound, wherein $R_1'$ is a halomagnesium group, is prepared in a conventional manner, for example by reacting a compound of the formula IV, IVa, VII or VIIb, wherein $R_1'$ is halo, for example chloro, bromo or iodo, with magnesium, e.g. in dry ether.

Unless stated otherwise, the conversion of a compound of the formula IV, IVa, VII or VIIb to a compound of the formula I, Ia, I* or Ib is preferably carried out in an inert, preferably anhydrous, solvent or solvent mixture, for example in a carboxylic acid amide, for example a formamide, for example dimethylformamide, a halogenated hydrocarbon, for example methylene chloride, carbon tetrachloride or chlorobenzene, a ketone, for example acetone, a cyclic ether, for example tetrahydrofuran, an ester, for example ethyl acetate, or a nitrile, for example acetonitrile, or in mixtures thereof, optionally in the presence of an alcohol, for example methanol or ethanol, or water, optionally at reduced or elevated temperature, for example in a temperature range from approximately −40° C. to approximately +100° C., preferably from room temperature to the boiling temperature of the reaction mixture and optionally under inert gas atmosphere, for example nitrogen atmosphere.

Process d)

In a starting material of the formula V or Vb, a leaving group $X_1$ is preferably esterified hydroxy, for example lower alkanoyloxy, for example acetoxy, or mesyloxy, benzenesulfonyloxy or toluenesulfonyloxy, or, especially, halogen, for example chlorine or bromine.

A suitable base is, for example, an alkali metal or alkaline earth metal hydroxide, e.g. a sodium, potassium or calcium hydroxide, a bicyclic amidine, for example 1,5-diazabicyclo[5.4.0]undec-5-ene, preferably an alcoholate, for example sodium or potassium methylate, ethylate or tert-butylate, an alkali metal amide, such as lithium diisopropylamide, or an alkali metal hydride, such as sodium hydride. If $R_2$ represents free or functionally modified carboxy or acyl, the reaction is remarkably facilitated and weaker bases, as for example tertiary amines, such as tri-lower alkylamines, e.g. triethylamine, can be used.

The cyclisation is carried out in an aprotic organic solvent, for example in an ether, for example diethyl ether, dioxan or tetrahydrofuran, or ketone, for example acetone, an amide, for example dimethylformamide or hexamethylphosphoric acid triamide, or in a mixture thereof, optionally also in a mixture of the mentioned solvents with an alkane, for example n-hexane or petroleum ether. The reaction temperature is between approximately −50° and 50° C., preferably between −10° and room temperature. The reaction is preferably carried out under an inert gas atmosphere, for example an argon or nitrogen atmosphere.

Process e)

In a starting material of the formula VI or VIb, a leaving group $X_2$ is preferably defined as a leaving group $X_1$ of process d). The cylcisation is carried out preferably by using a base, such as tertiary amine as defined above, e.g. triethylamine, or even using no base at all. NH protecting (or blocking) group $R_o$ are preferably tri-lower alkylsilyl, such as trimethylsilyl, lower alkanoyl, such as acetyl, dialkylcarbamoyl, such as dimethylcarbamoyl, or triphenylmethyl.

Process g)

The non-reductive reaction is preferably performed in the presence of an acidic catalyst, e.g. p-toluenesulfonic acid. The reductive amination reaction is e.g.

performed with hydrogen in the presence of an usual hydrogenation catalyst, such as Raney nickel, platinum or palladium on charcoal, or with a hydrogen-supplying agent, e.g. sodium cyanoborohydride.

Process h)

The decarboxylation reaction can be performed with usual decarboxylation means, e.g. acids, such as hydrochloric acid, preferably at elevated temperatures.

Subsequent Reactions

A compound of the formula I, Ia, Id or Ie can be converted to a hydrogenated derivative of formula I*, the corresponding 5,6,7,8-tetrahydro derivatives, e.g. of the formula Ib wherein $R_2$ is hydrogen, by reduction, e.g. with hydrogen in the presence of a hydrogenation catalyst, e.g. palladium, under acid conditions, for example in a mineral acid, for instance hydrochloric acid, in an inert solvent, e.g. ethanol or ethyl acetate.

Furthermore, compounds of formula I* or Ib wherein $R_2$ is carboxy, can be decarboxylated in order to obtain another compound of formula I* or Ib wherein $R_2$ is hydrogen using usual decarboxylation procedures, e.g. those described above for process h). In said compounds of formula I*, the carboxy substituent $R_2$ is preferably bonded to the same carbon atom as the substituent $C_6H_4$-$R_1$.

A compound of formula I* in which the carbon atom adjacent to the ring junction nitrogen is monosubstituted by $C_6H_4$-$R_1$, e.g. a compound of formula Ib or Ic wherein $R_2$ represents hydrogen, can be further substituted on the same carbon atom with groups represented by $R_2$ by condensation under basic conditions with a reactive derivative of $R_2$, for example, a lower alkyl halide, an aryl-lower alkyl halide or a lower alkyl disulfide. Suitable bases comprise an alkali metal alkoxide, such as potassium t-butoxide, an alkali metal amide, such as lithium diisopropylamide, or an alkali metal hydride, such as sodium hydride.

Preparation of the Intermediates

Compounds of the formula II and IIa are known or if they are novel, they can be prepared according to known methods, for example by reacting a compound of the formula VIII or VIIIa

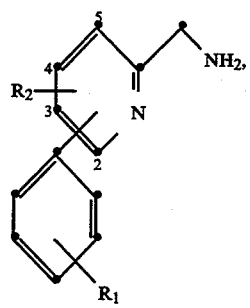

(VIII)

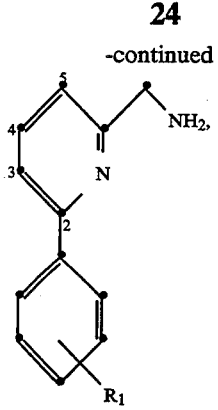

(VIIIa)

wherein $R_1$ and $R_2$ are as defined above under formula I or Ia, with formic acid or a reactive, functional derivative thereof, e.g. formic acetic anhydride.

Compounds of the formula III and IIIa are prepared e.g. by reacting a compound of formula V, wherein $X_1$ is hydroxy, n denotes 2, $R_2'$ is as defined under formula V and represents preferably hydrogen, and $R_2''$ is hydrogen, or a compound of formula Vb, wherein $X_1$ is hydroxy and $R_2$ is hydrogen, with e.g. dimethylsulfoxide in the presence of dehydrating agents, for example acid anhydrides, for example anhydrides of organic carboxylic acids, such as aliphatic or aromatic carboxylic acids or dicarboxylic acids, for example anhydrides of lower alkanecarboxylic acids, especially acetic acid anhydride, mixed anhydrides of lower alkane carboxylic or dicarboxylic acids with mineral acids, for example acetyl- or oxalyl-chloride, as well as anhydrides of inorganic acids, especially of phosphoric acid, such as phosphorus pentoxide. The above anhydrides, above all of organic carboxylic acids, for example oxalyl chloride, are preferably used in an approximately 1:1 mixture with dimethyl sulfoxide. Further dehydrating or water-absorbing agents are carbodiimides, above all dicyclohexylcarbodiimide, as well as diisopropylcarbodiimide, or keteneimides, for example diphenyl-N-p-tolylkeneneimide; these reagents are preferably used in the presence of acid catalysts, such as phosphoric acid or pyridinium trifluoroacetate or pyridinium phosphate. Sulfur trioxide can also be used as a dehydrating or water-absorbing agent, in which case it is customarily employed in the form of a complex, for example with pyridine. A base is subsequently added, preferably a base which has been mentioned above under process c), for example triethylamine.

The compounds of the formula IV and IVa are prepared preferably analogous to process a) mentioned above.

Compounds of the formula V and Vb are known or if they are novel, they can be prepared according to known methods, for example by reacting another compound of the formula V or Vb, wherein $X_1$ is hydroxy and wherein both $R_2'$ and $R_2''$ are, or $R_2$ is, preferably hydrogen, with a halogenating agent or by esterifying the hydroxy group with a reactive functional derivative of a sulfonic acid or carboxylic acid. Said reaction with a halogenating agent, such as thionyl chloride or phosphorous pentachloride, is carried out in a manner analogous to the halogenation process as described in U.S. Pat. No. 4,089,955. Said reaction with a reactive functional derivative of a sulfonic or carboxylic acid, for example a mixed anhydride with a mineral acid, for example mesylchloride, benzenesulfonyl chloride or p-toluenesulfonylchloride, or acetyl chloride, is carried out by known esterification methods.

Compounds of the formula VI and VIb are known or if they are novel, they can be prepared according to known methods, for example by reacting another compound of the formula VI or VIb, wherein $X_2$ is hydroxy, $R_1$ and $R_2$ are as defined above under formula I* or Ib, and the imidazole NH group is optionally protected by a conventional amino protecting group, e.g. tri-lower alkylsilyl, such as trimethylsilyl, with a halogenating agent or by esterifying the hydroxy group with a reactive, functional derivative of a sulfonic acid or a carboxylic acid. $R_2$ is preferably lower alkyl and especially hydrogen. Said halogenation reaction is carried out analogously to the process according to U.S. Pat. No. 4,089,955. Said reaction with a reactive, functional derivative of a sulfonic or carboxylic acid, for example a mixed anhydride with a mineral acid, for example mesylchloride, benzenesulfonyl chloride or p-toluenesulfonylchloride, or acetyl chloride, is carried out by known esterification methods.

The compounds of the formula VII or VIIb are prepared preferably analogous to processes d) and e), and also g) and h), mentioned above.

Compounds of the formula VIII or VIIIa are known or if they are novel, they can be prepared according to known methods, for example by hydrogenation of a compound of the formula XV or XVa

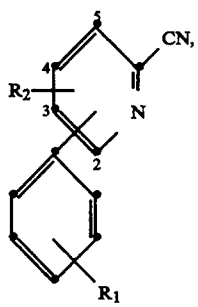

(XV)

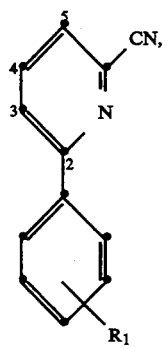

(XVa)

wherein $R_1$ and $R_2$ are as defined above under formula I or Ia.

The hydrogenation is preferably carried out in the presence of a catalyst, for example platinum or palladium on charcoal, in the presence of a mineral acid, for example hydrochloric acid.

Compounds of the formula V or Vb, wherein $X_1$ is hydroxy, are known or if they are novel, they can be prepared according to known methods, for example by reacting a compound of the formula XVII or XVIIa

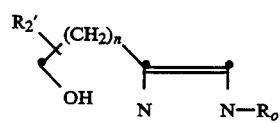

(XVII)

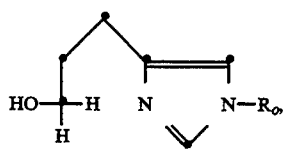

(XVIIa)

wherein n and $R_2'$ are defined as n and $R_2$ under formula I*, $R_o$ is a NH blocking group as defined above, for example di-lower alkylated carbamoyl, such as dimethylcarbamoyl, and the hydroxy group is protected by a conventional hydroxy protecting group, for example trimethylsilyl, with a compound of the formula XVIII or XVIIIa

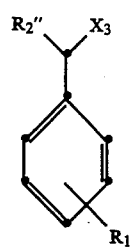

(XVIII)

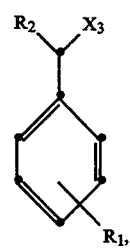

(XVIIIa)

wherein $R_1$ is as defined under formula I or Ia, $R_2$ is as defined under formula Ib, preferably hydrogen, $R_2''$ is defined as $R_2$ under formula I*, and $X_3$ is a leaving group, for example esterified hydroxy, for example halogen, for example chlorine or bromine, or sulfonyloxy, for example mesyloxy or p-toluenesulfonyloxy.

Compounds of the formula VI and VIb, wherein $X_2$ is hydroxy, $R_2$ preferably is lower alkyl and especially hydrogen and the radical $C_6H_4$-$R_1$ is bonded to the same carbon atom as the group $X_2$, are known or if they are novel, they can be prepared according to known methods for example by reacting a compound of the formula XIX or XIXa

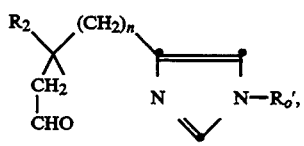

(XIX)

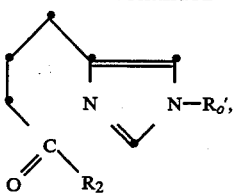

(XIXa)

wherein n and $R_2$ are as defined above under formula I* or Ib, and $R_2$ is preferably lower alkyl and especially hydrogen, in formula XIX it being possible for the group $R_2$ to substitute any of the carbon atoms indicated inclusive the carbonyl carbon, and wherein $R_o'$ represents preferably a conventional NH protecting group as defined above, e.g. tri-lower alkylsilyl, such as trimethylsilyl, in an organometallic type reaction with a compound of the formula XX

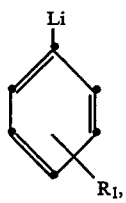

(XX)

wherein $R_1$ is as defined under formula I or Ia.

Compounds of the formula XV and XVa can be prepared e.g. by converting a compound of the formula XXI or XXIa

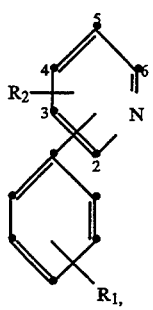

(XXI)

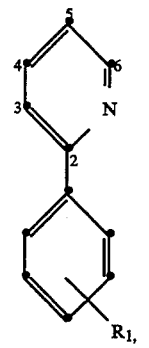

(XXIa)

to the N-oxide with an oxidizing agent, e.g. peracetic acid, treating the N-oxide with a methylating agent, e.g. dimethyl sulfate and substituting the 6-position with a cyanide ion, e.g. by using potassium cyanide.

Compounds of the formulae XVII-XXI, XVIIa-XIXa and XXIa are known or may be prepared using conventional chemical methodology.

Compounds of formula IX and IXb can be prepared e.g. by the following sequence of transformations: Oxidation of a compound of formula XIX—or formula XIXa, wherein $R_2$ is hydrogen—with usual oxidations means, e.g. $KMnO_4$, yields the corresponding acid which optionally can be converted further to the corresponding lower alkylester. Reacting the latter—or the free acid—with a compound of formula XX, or a suitable organometallic equivalent thereof, and splitting off the NH protecting group leads to compounds of formula IXb and IX, in the latter of which the substituent $C_6H_4$-$R_1$ is bonded to the carbonyl carbon.

Compounds of formula VI and IX, wherein the substituent $C_6H_4$-$R_1$is not bonded to the same carbon atom as the group $X_2$ or to the carbonyl carbon respectively, can be obtained e.g. from compounds analogous to formula XVII containing in addition a substituent $C_6H_4$-$R_1$ in the side chain according to well-known procedures, e.g. by esterification of the hydroxy group or its oxidation to formyl respectively. The starting materials analogous to formula XVII can be prepared using conventional chemical methodology.

Starting materials for process h) containing a carboxy group in 3- or 1-position of the bicyclic ring system can be obtained e.g. by reacting a compound of formula VIII or VIIIa, or a compound analogous to these formulae containing an additional carboxy group in α-position respectively, with e.g. oxalic acid lower alkylester halide, such as ethyl oxalyl chloride, or with a formic acid derivative, e.g. formic acetic anhydride, and subsequent ringclosure achieved by a Lewis acid, e.g. phosphorous oxychloride, respectively.

If any intermediates mentioned interfering reactive groups, e.g. carboxy, hydroxy, amino, sulfo or mercapto groups, such may advantageously be temporarily protected at any stage with easily removable protecting groups. The choice of protecting groups for a particular reaction depends on several factors, e.g. the nature of the functional group to be protected, the structure and stability of the molecule of which the substituent is the functional group, and the reaction conditions. Protecting groups that meet these conditions and their introduction and removal are known to the art and are described, for example, in J. F. W. McOmie, "Protective Groups in Organic Chemistry", Plenum Press, London, New York 1973. Thus, carboxy groups and also sulfo groups, are protected, for example, in esterified form, e.g. as unsubstituted or substituted lower alkyl esters, such as methyl or benzyl esters, it being possible for such ester groupings to be removed easily under mild conditions, especially alkaline conditions. Amino- and hydroxy-protecting groups that can be removed under mild conditions are for example acyl radicals, such as lower alkanoyl optionally substituted by halogen, e.g. formyl or trichloroacetyl, or organic silyl, e.g. tri-lower alkylsilyl, such as trimethylsilyl.

Salts of compounds of the invention can be manufactured in a manner known per se. Thus, they can be formed e.g. in accordance with the methods described in the Examples. Acid additional salts of compounds of the invention are obtained in customary manner, for example by treating the free compound with an acid or a suitable anion exchange reagent. Salts can be converted into the free compounds in a customary manner, for example by treating the acid addition salt with a suitable basic agent, for example an alcoholate, e.g. potassium-tert-butoxide. On the other hand, compounds of the invention containing acidic groups, e.g. carboxy, can be converted into salts in a manner known per se by treating with a base, e.g. an alkali metal hydroxide or alkoxide, an alkali metal or alkaline-earth metal salt, e.g. sodium hydrogen carbonate, ammonia or a suitable organic amine. The free compounds can be obtained by treating such salts with an acid. In view of the close relationship between the free compounds and the compounds in the form of their salts, whenever a compound is referred to in this context, a corresponding salt is also intended, provided such is possible or appropriate under the circumstances.

Depending on the choice of starting materials and methods, the new compounds may be in the form of one of the possible isomers or mixtures thereof, for example, depending on the presence of chiral carbon atoms, as optical isomers, such as antipodes, or as mixtures of optical isomers, such as racemates, or as mixtures of diastereoisomers.

Resulting mixtures of diastereoisomers can be separated on the basis of the physicochemical differences of the constituents, for example by chromatography and/or fractional crystallisation.

Resulting racemates can furthermore be resolved into the optical antipodes by known methods, for example by chromatography using an optically active stationary phase, by recrystallisation from an optically active solvent, by means of microorganisms or by reacting an acidic intermediate or final product with an optically active base that forms salts with the racemic acid, and separating the salts obtained in this manner, for example on the basis of their different solubilities, into the diastereoisomers, from which the antipodes can be liberated by the action of suitable agents. Basic racemic products can likewise be resolved into the antipodes, for example, by separation of diastereoisomeric salts thereof, e.g. by the fractional crystallization of d- or l-tartrates.

The above-mentioned reactions are carried out according to standard methods, in the presence or absence of diluents, preferably such as are inert to the reagents and are solvents thereof, of catalysts, condensing or said other agents respectively and/or inert atmospheres, at low temperatures, room temperature or elevated temperatures, e.g. in a temperature range from $-20°$ to $+200°$ C., preferably at the boiling point of the solvents used, and at atmospheric or super-atmospheric pressure. The preferred solvents, catalysts and reaction conditions are set forth in the appended illustrative examples.

The compounds, including their salts, can also be obtained in the form of their hydrates, or include other solvents used for their crystallization.

The invention further includes any variant of the present processes, in which an intermediate product obtainable at any stage thereof is used as starting material and the remaining steps are carried out, or the process is discontinued at any stage thereof, or in which the starting materials are formed under the reaction conditions or in which the reaction components are used in the form of their salts or optically pure antipodes. Mainly those starting materials should be used in said reactions, that lead to the formation of those compounds indicated above as being especially useful. The invention also relates to novel starting materials and processes for their manufacture.

The invention further relates to pharmaceutical compositions for enteral or parenteral administration, which compositions comprise a therapeutically effective amount of a compound of the invention optionally together with a pharmaceutically acceptable carrier or mixture of carriers. Solid or liquid inorganic or organic substances are used as carriers. Appropriate dosage unit formulations, especially for peroral administration, e.g. tablets or capsules, preferably contain about 5 mg to 200 mg. preferably 5 mg to 100 mg, most preferably about 10 to 50 mg, of a compound off the invention, or of a pharmaceutically acceptable salt of such a compound which is capable of salt formation, together with pharmaceutically acceptable carriers.

Suitable carriers are in particular fillers such as sugar, for example lactose, saccharose, mannitol or sorbitol, cellulose preparations and/or calcium phosphates, e.g. tricalcium phosphate or calcium biphosphate, and also binders such as starch pastes, e.g. maize, corn, rice or potato starch, gelatin, tragacanth, methyl cellulose and/or, if desired, disintegrators, such as the above mentioned starches, also carboxymethyl starch, crosslinked polyvinylpyrrolidone, agar, alginic acid or a salt thereof such as sodium alginate. Adjuncts are in particular glidants and lubricants, for example silica, talc, stearic acid or salts thereof such as magnesium stearate or calcium stearate, and/or polyethylene glycol. Dragee cores are provided with suitable coatings which can be resistant to gastric juices, using inter alia concentrated sugar solutions which may contain gum arabic, talc, polyvinylpyrrolidinone, polyethylene glycol and/or titanium dioxide, shellac solutions in suitable organic solvents or mixtures of solvents or, for the preparation of coatings which are resistant to gastric juices, solutions of suitable cellulose preparations such as acetyl cellulose phthalate or hydroxypropylmethylcellulose phthalate. Dyes or pigments can be added to the tablets or dragee coatings, for example to identify or indicate different doses of the active ingredient.

Further pharmaceutical compositions for oral administration are dry-filled capsules made of gelatin and also soft sealed capsules consisting of gelatin and a plasticiser such as glycerol or sorbitol. The dry-filled capsules can contain the active ingredient in the form of granules, for example in admixture with fillers such as lactose, binders such as starches and/or glidants such as talc or magnesium stearate, and optionally stabilisers. In soft capsules, the active ingredient is preferably dissolved or suspended in suitable liquids, such as fatty oils, paraffin oil or liquid polyethylene glycols, to which stabilisers can also be added.

Suitable pharmaceutical compositions for rectal administration are e.g. suppositories, which consist of a combination of the active ingredient with a suppository base. Examples of suitable suppository bases are natural or synthetic triglycerides, paraffin, polyethylene glycols and higher alkanols. It is also possible to use gelatin rectal capsules which contain a combination of the active ingredient with a base material. Suitable base materials are e.g. liquid triglycerides, polyethylene glycols and paraffins.

Particularly suitable dosage forms for parenteral administration are suspensions of the active ingredient, such as corresponding oily injection solutions of suspensions, for which are used suitable lipophilic solvents or vehicles such as fatty oils, for example sesame oil, or synthetic fatty acid esters, for example ethyl oleate or triglycerides, or aqueous injection suspensions or solutions which contain substances which increase the viscosity, for example sodium carboxymethylcellulose, sorbitol and/or dextran, and optionally also stabilizers.

The pharmaceutical compositions of the present invention are prepared in a manner known per se, for example by conventional mixing, granulating, confectioning, dissolving or lyophilising methods. For example, pharmaceutical compositions for oral administration can be obtained by combining the active ingredient with solid carriers, optionally granulating a resulting mixture and processing the mixture of granulates, if desired or necessary after the addition of suitable adjuncts, to tablets or dragee cores.

The present invention also relates to a method of inhibiting aromatase activity in mammals by administering an effective aromatase inhibiting amount of a compound of the invention, e.g. of formula I, I*, Ia, Ib or Id or a pharmaceutically acceptable salt thereof, or of a pharmaceutical composition comprising said compound, to a mammal in need thereof.

The present invention is thus also directed to the method of treatment in mammals of conditions responsive to aromatase inhibition, e.g. gynecomastia and estrogen dependent diseases, e.g. estrogen dependent tumors such as breast carcinoma, by administering an effective aromatase inhibiting amount of a compound of the invention, or of a pharmaceutical composition comprising such compound, to a mammal in need thereof.

A further aspect of the invention relates to a method of inhibiting thromboxane synthetase in mammals and for treating conditions responsive to thromboxane synthetase inhibition in mammals, by administering an effective thromboxane synthetase inhibiting amount of a compound of the invention, or of a pharmaceutical composition comprising said compound to a mammal in need thereof.

EXAMPLES

The following examples are intended to illustrate the invention and are not to be construed as being limitations thereon. Temperatures are given in degrees Centigrade, and all parts wherever given are parts by weight. If not mentioned otherwise, all evaporations are performed under reduced pressure, preferably between about 15 and 100 mm Hg.

EXAMPLE 1

5-(p-Cyanophenyl)-5,6,7,8-tetrahydroimidazo[1,5-a]-pyridine hydrochloride

A solution of 8.1 g of 5-(3-chloropropyl)-1-(p-cyanophenylmethyl)-1H-imidazole in 50 ml of tetrahydrofuran is cooled to 0°. To this is added 7.0 g of potassium t-butoxide as a solid in portions. The mixture is stirred at room temperature for 2 h, neutralized with 10% acetic acid and partitioned between methylene chloride and water. The organic layer is washed with water, dried over magnesium sulfate and evaporated to yield an oil which is dissolved in a small volume of acetone and neutralized with ethereal hydrogen chloride. On cooling, the title compound is obtained as a white solid, m.p. 201°–203°.

Preparation of the starting materials:

a)
1-Dimethylcarbamoyl-4-(3-trimethylsilyloxypropyl)-1H-imidazole

To a suspension of 51.8 g of 4-(3-hydroxy-n-propyl)-1H-imidazole [obtainable according to Il Farmaco, Ed. Sc. 29, 309 (1973)] in 500 ml of acetonitrile 50.0 g of triethylamine is added. To this mixture 48.6 g of dimethylcarbamoyl chloride is added dropwise. When addition is complete, the mixture is refluxed for 21 h. The solution is cooled to 0°, whereupon there is precipitation of triethylamine hydrochloride. To this mixture is added 50.0 g of triethylamine followed by 54.0 g of chlorotrimethylsilane. After addition is complete stirring is continued for 1 h. The mixture is diluted with an equal volume of ether and filtered. The filtrate is evaporated to an oil which is triturated with ether and filtered to remove additional triethylamine hydrochloride. This filtrate is then evaporated to yield the title compound a) as an oil.

b)
1-(p-Cyanophenylmethyl)-5-(3-hydroxypropyl)-1H-imidazole

A solution of 97.0 g of 1-dimethylcarbamoyl-4-(3-trimethylsilyloxypropyl)-1H-imidazole and 72.0 g of 1-bromomethyl-4-cyanobenzene in 500 ml of acetonitrile is refluxed for 10 h. The solution is cooled to 0° in an ice bath and ammonia gas is bubbled in for a few minutes. The mixture is then evaporated in vacuo to give a semi-solid which is dissolved in 500 ml of 1N hydrochloric acid. The solution is allowed to stand at room temperature for 15 min and then is extracted with ether. The pH of the aqueous phase is adjusted to 9 with 50% sodium hydroxide solution and the mixture is then extracted with methylene chloride. The methylene chloride extracts are washed with water, dried over sodium sulfate and evaporated to give a semi-solid which is triturated with cold acetone to yield the title compound b) as a white solid, m.p. 121°–123°.

c)
5-(3-Chloropropyl)-1-(p-cyanophenylmethyl)-1H-imidazole

To a solution of 5.2 g of thionyl chloride in 80 ml of methylene chloride is added 8.4 g of 1-(p-cyanophenylmethyl)-5-(3-hydroxypropyl)-1H-imidazole as a solid in portions. The rate of addition is regulated to control the foaming that occurs. When addition is complete, the solution is refluxed for 1.5 h, cooled in ice and filtered to obtain the hydrochloride salt of the title compound c) as a buff-colored solid, m.p. 190°–191°. The salt is partitioned between methylene chloride and saturated sodium bicarbonate solution. The organic extracts are washed with water, dried over sodium sulfate and evaporated to yield the free base as an oil.

EXAMPLE 2

5-(p-Cyanophenyl)-5,6,7,8-tetrahydroimidazo[1,5-a]-pyridine hydrochloride

A solution of 2.0 g of 4-[4-chloro-4-(p-cyanophenyl)-n-butyl]-1H-imidazole in 50 ml of chloroform is refluxed for 4 h under nitrogen, cooled and evaporated to yield the title compound.

Preparation of the starting materials:

a) 4-(3-Formyl-n-propyl)-1-trimethylsilylimidazole

A solution of 1.82 g of 4-(3-ethoxycarbonylpropyl)-1H-imidazole in 30 ml of tetrahydrofuran under nitrogen is treated with 0.5 g of sodium hydride (50% oil dispersion) at 0° for 30 min and 1.45 ml of trimethylsilyl chloride at 0° for 3 h. The reaction mixture is washed with cold 0.5N sodium bicarbonate solution, dried over sodium sulfate and evaporated to dryness. The oil is redissolved in 100 ml of methylene chloride at −78° under nitrogen and 12.82 ml of diisobutylaluminium hydride (1.56M) is added dropwise. The reaction mixture is stirred for 5 min at −78°, quenched with 1 ml of methanol followed by 10 ml of water and filtered through Celite ®. The organic phase is separated, dried over sodium sulfate and evaporated to yield the title compound a).

b)
4-[4-(p-tert-Butylaminocarbonylphenyl)-4-hydroxy-n-butyl]-1-trimethylsilylimidazole A solution of 6.95 g of p-(tert-butylaminocarbonyl)-bromobenzene is dissolved in 175 ml of tetrahydrofuran at −70° under nitrogen and 20.1 ml of a solution of n-butyllithium (2.7M) in hexane is added dropwise. After reacting 30 min, a solution of 5.69 g of 4-(3-formyl-n-propyl)-1-trimethylsilylimidazole in 10 ml of tetrahydrofuran is added slowly. The reaction mixture is allowed to warm slowly to room temperature and 20 ml of ammonium chloride is added. The organic layer is separated, dried over sodium sulfate and evaporated to yield the title compound b).

c)
4-[4-Chloro-4-(p-cyanophenyl)-n-butyl]-1H-imidazole

A solution of 4,5 g of 4-[4-(p-tert-butylaminocarbonylphenyl)-4-hydroxy-n-butyl]-1-trimethylsilylimidazole in 50 ml of thionyl chloride is refluxed for 1 h, cooled and evaporated. The residue is partitioned between methylene chloride and aqueous sodium bicarbonate solution. The organic phase is separated, dried over sodium sulfate and evaporated to yield the title compound c).

EXAMPLE 3

5-(p-Cyanophenyl)imidazo[1,5-a]pyridine

A solution of 0.1 g of 5-(p-tert-butylaminocarbonylphenyl)imidazo[1,5-a]pyridine in 3 ml of toluene is treated with 40 μl of phosphorus oxychloride at 90° for 5 h. The solvent is evaporated and the residue is redissolved in 30 ml of chloroform at 0°. An ice-cold ammonium hydroxide solution is added and the organic phase is separated, dried over sodium sulfate and evaporated. The residue is chromatographed on silica with ethyl acetate to yield the title compound, m.p. 117°–118°.

EXAMPLE 4

5-(p-Ethoxycarbonylphenyl)imidazo[1,5-a]pyridine

A solution of 9.8 g of 2-(p-ethoxycarbonylphenyl)-6-formylaminomethylpyridine and 11.15 g phosphorus oxychloride in 26 ml of toluene is heated at 90° for 15 h. The solvent is evaporated and the residue taken up in 50 ml of methylene chloride, cooled at 0° and made basic with excess ice-cold, saturated ammonium hydroxide solution. The organic phase is separated, dried and evaporated. The residual solid is passed through 100 g of silica gel with ethyl acetate as eluent to yield after crystallization the title compound, m.p. 118°–119°.

Preparation of the starting materials:

a) 6-Cyano-2-(p-ethoxycarbonylphenyl)pyridine 8.9 ml of 40% peracetic acid is added dropwise to 14.08 g of 2-(p-ethoxycarbonylphenyl)pyridine so as to maintain the reaction temperature between 80° and 85°. After the addition is complete the reaction mixture is heated at 90° for 3 h, and allowed to cool to room temperature. The excess peracetic acid is destroyed with aqueous sodium sulfite solution. The solvent is evaporated and the residue taken up in methylene chloride and refiltered through Celite ®. Evaporation yields 2-(p-ethoxycarbonylphenyl)pyridine-N-oxide which is treated with 8.66 g dimethyl sulfate in 62 ml of toluene at 90° for 3 h. The solvent is evaporated and the residue redissolved in an ice-cold mixture of 8 ml of water and 9.3 ml of 1N sodium hydroxide. A solution of 13.64 g of potassium cyanide in 10 ml of water is added slowly and the reaction mixture is maintained at 0° for 24 h. Extraction with methylene chloride, drying over sodium sulfate and evaporation of solvent yields the title compound a); IR (CH$_2$Cl$_2$) 2200 cm$^{-1}$.

b)
6-Aminomethyl-2-(p-ethoxycarbonylphenyl)pyridine 16.23 g of 6-cyano-2-(p-ethoxycarbonylphenyl)pyridine is hydrogenated at atmospheric pressure in 254 ml of methanol with 12.9 ml of concentrated hydrochloric acid and 2.63 g of 10% palladium on charcoal until 2 molar equivalents of hydrogen have been consumed. Sodium methoxide (6.9 g) is added and the catalyst is filtered off. The solvent is evaporated. The residue is redissolved in 20 ml of methylene chloride and the salts are removed by filtration. Evaporation of the solvent yields a solid which is recrystallised from chloroform to yield the title compound b), m.p. 141°–143°.

c)
2-(p-Ethoxycarbonylphenyl)-6-formylaminomethylpyridine

A solution of 0.76 g 6-aminomethyl-2-(p-ethoxycarbonylphenyl)pyridine in 10 ml of formic acid is heated at 90° for 15 h. The reaction mixture is cooled to 0°, made basic with excess saturated ammonium hydroxide solution and extracted with chloroform. The organic extracts are dried and evaporated to yield the title compound c) which is recrystallised from toluene, m.p. 119.5°–120.5°.

EXAMPLE 5

5-(p-Carboxyphenyl)imidazo[1,5-a]-pyridine

A solution of 1.18 g or 5-(p-ethoxycarbonylphenyl)imidazo[1,5-a]pyridine in 10 ml of ethanol and 14 ml of 1N sodium hydroxide solution is refluxed for 3 h, cooled and evaporated. The residue is partitioned between water and ethyl acetate. The aqueous phase is separated and adjusted to pH 5. The solid is filtered, washed with water and dried to yield the title compound, m.p. 308°–310° (dec.).

EXAMPLE 6

5-(p-tert-Butylaminocarbonylphenyl)imidazo[1,5-a]pyridine

To a slurry of 0.4 g of 5-(p-carboxyphenyl)imidazo[1,5-a]pyridine in 40 ml of methylene chloride under nitrogen at room temperature, is added 30 μl of N,N-dimethylformamide followed by 0.16 ml of oxalyl chloride. The reaction mixture is stirred until gas evolution is complete and 0.46 ml of tert-butylamine is added dropwise. Stirring is discontinued after 90 min and 10 ml of saturated sodium bicarbonate solution is added. The organic layer is separated, dried over sodium sulfate and evaporated to yield the title compound, m.p. 128°–131°.

EXAMPLE 7

5-(p-Cyanophenyl)-5,6,7,8-tetrahydroimidazo[1,5-a]pyridine hydrochloride

A solution of 1.13 g of 5-(p-carbamoylphenyl)-5,6,7,8-tetrahydroimidazo[1,5-a]pyridine and 1.0 ml of phosphorus oxychloride in 30 ml of chloroform is refluxed for 15 h, cooled and evaporated with toluene. The resulting oil is redissolved in 30 ml of methylene chloride, cooled to 0° and 30 ml of an ice-cold solution of 50% ammonium hydroxide solution is added. The organic phase is separated, dried and evaporated to an oil. Filtration through 20 g of silica with ethyl acetate yields the free title compound which is dissolved in 20 ml of acetone and treated with 1.2 ml of 3N ethereal hydrogen chloride to yield its hydrochloride, m.p. 209°–210°.

EXAMPLE 8

5-(p-Ethoxycarbonylphenyl)-5,6,7,8-tetrahydroimidazo[1,5-a]pyridine hydrochloride A solution of 2.0 g of 5-(p-ethoxycarbonylphenyl)imidazo[1,5-a]pyridine in 120 ml of anhydrous ethanol containing 30 ml of concentrated hydrochloric acid, is hydrogenated with 1.0 g of 10% palladium on charcoal at 40 psi hydrogen and 60° for 4 h. The catalyst is filtered and the solvent is evaporated to yield a solid which is recrystallized from isopropanol and ether to provide the title compound, m.p. 164°–166°.

EXAMPLE 9

5-(p-Carboxyphenyl)-5,6,7,8-tetrahydroimidazo[1,5-a]pyridine

A solution of 0.66 g of 5-(p-ethoxycarbonylphenyl)-5,6,7,8-tetrahydroimidazo[1,5-a]pyridine in 8.0 ml of ethanol and 8.0 ml 1N sodium hydroxide is refluxed for 3 h, cooled and evaporated. The residue is partitioned between water and ethyl acetate. The aqueous phase is adjusted to pH 5 with concentrated sulfuric acid and the solid is filtered and air-dried to yield the title compound, m.p. 309°–310° (dec.).

EXAMPLE 10

5-(p-Carbamoylphenyl)-5,6,7,8-tetrahydroimidazo[1,5-a]pyridine

A solution of 5.42 g of 5-(p-carboxyphenyl)-5,6,7,8-tetrahydroimidazo[1,5-a]pyridine in 75 ml of thionyl chloride is refluxed for 30 min, cooled and evaporated with toluene. The residue is redissolved in methylene chloride, cooled to 0° and treated with gaseous ammonia until the solution is saturated. The reaction mixture is stirred for 10 min under an ammonia atmosphere and the resulting solid is collected by filtration to yield the title compound, m.p. 181°–183°. Treatment with a molar equivalent of fumaric acid in ethanol yields the fumarate salt, m.p. 164°–166° (dec.).

EXAMPLE 11

5-(p-Tolyl)-5,6,7,8-tetrahydroimidazo[1,5-a]pyridine hydrochloride

A solution of 0.36 g of 5-(p-hydroxymethylphenyl)imidazo[1,5-a]pyridine in 25 ml of ethanol and 6.4 ml of concentrated hydrochloric acid is hydrogenated with 0.15 g of 10% palladium on charcoal at 40 psi of hydrogen and 60° for 4 h. The reaction mixture is filtered and evaporated and the residue is partitioned between methylene chloride and sodium bicarbonate solution. The organic phase is dried over sodium sulfate and evaporated to an oil which is purified by preparative layer chromatography on silica with ethyl acetate. The hydrochloride salt is prepared in acetone with 1.1 molar equivalents of ethereal hydrogen chloride to yield the title compound, m.p. 173°–175°.

EXAMPLE 12

5-(p-Hydroxymethylphenyl)imidazo[1,5-a]pyridine 1 g of 5-(p-ethoxycarbonylphenyl)imidazo[1,5-a]pyridine is dissolved in 26 ml of methylene chloride at −78° under nitrogen, and then 6.6 ml of diisobutylaluminium hydride in toluene (11.4 mmole) is added dropwise. After stirring for 1 h, 1.5 ml of methanol is added, the cold bath is removed and 15 ml of water is added. The salts are filtered off, the organic phase is dried over sodium sulfate and evaporated to yield the title compound, m.p. 137°–138°.

EXAMPLE 13

5-(p-Cyanophenyl)-7,8-dihydroimidazo[1,5-a]pyridine

A solution of 0.24 g of 1-(p-cyanophenylmethyl)-5-(2-formylethyl)-1H-imidazole in 10 ml of anhydrous ethanol is refluxed under nitrogen for 2 h with 20 mg of potassium tert-butoxide, cooled and evaporated to yield the title compound.

Preparation of the starting material:

a) 1-(p-Cyanophenylmethyl)-5-(2-formylethyl)-1H-imidazole

A solution of 0.14 ml of dimethylsulfoxide in 5 ml of methylene chloride is cooled to −78° under N$_2$ and 0.1 ml of oxalyl chloride is added dropwise. After 30 min, a solution of 0.24 g of 1-(p-cyanophenylmethyl)-5-(3-hydroxypropyl)-1H-imidazole in 1 ml of methylene chloride and 0.2 ml of dimethylsulfoxide is added slowly. The reaction mixture is stirred at −78° for 2 h and 1 ml of triethylamine is added slowly. The reaction mixture is allowed to warm slowly to room temperature, diluted with 30 ml of methylene chloride and washed three times with 10 ml of water. The organic phase is dried over sodium sulfate and evaporated to yield the title compound a) as an oil, NMR (60 MHZ): δ5.15 (s, 2H), 9.65 (s, 1H).

EXAMPLE 14

5-(p-Cyanophenyl)-5,6,7,8-tetrahydroimidazo[1,5-a]pyridine

A solution of 1.6 g of 5-(p-cyanophenyl)-7,8-dihydroimidazo[1,5-a]pyridine in 50 ml of ethyl acetate is hydrogenated at atmospheric pressure with 0.2 g of 5% palladium on charcoal until the theoretical uptake of hydrogen is complete. The catalyst is filtered, and the solvent evaporated to yield the title compound, m.p. 117°–118°.

EXAMPLE 15

5-(p-Cyanophenyl)-5,6,7,8-tetrahydroimidazo[1,5-a]pyridine

A solution of 54 mg of 5-(p-cyanophenyl)imidazo[1,5-a]pyridine hydrochloride in 5.0 ml methanol is hydrogenated at room temperature and atmospheric pressure for 30 min with 0.1 g of 10% palladium on charcoal. The catalyst is filtered and 0.21 ml of 1N sodium hydroxide is added. The filtrate is evaporated, taken up in 10 ml of methylene chloride and filtered through Celite®. Evaporation yields an oil which is chromatographed on silica gel with ethyl acetate to yield the title compound, m.p. 117°–118°.

EXAMPLE 16

5-(p-Cyanophenyl)-5,6,7,8-tetrahydroimidazo[1,5-a]pyridine

A mixture of 85 mg of 5-(p-bromophenyl)-5,6,7,8-tetrahydroimidazo[1,5-a]pyridine and 74 mg of cuprous cyanide in 1 ml of N,N-dimethylformamide is heated under nitrogen at 120° for 11 h. The reaction mixture is cooled, diluted with 10 ml of water and extracted with ethyl acetate. The organic extracts are dried over sodium sulfate and evaporated. The resulting oil is chromatographed on silica gel with ethyl acetate to yield the title compound, m.p. 117°–118°.

EXAMPLE 17

5-(p-Bromophenyl)-5,6,7,8-tetrahydroimidazo[1,5-a]pyridine

A solution of lithium diisopropylamine, prepared at 0° from 0.12 ml of diisopropylamine and 0.33 ml of n-butyllithium (2.5M) in 2 ml of tetrahydrofuran under nitrogen, is added to a solution of 0.13 ml of N,N,N',N'-tetramethyl-ethylenediamine and 0.124 g of 1-(p-bromobenzyl)-5-(3-chloropropyl)-1H-imidazole in 2 ml of tetrahydrofuran at −78°. The reaction mixture is stirred for 3.5 h, quenched at −78° with saturated ammonium chloride solution and extracted with methylene chloride (3×10 ml). The organic extracts and dried over sodium sulfate and evaporated to yield the title compound which is purified by conversion to the hydrochloride salt, m.p. 216°.

Preparation of the starting materials:

a) 1-(p-Bromobenzyl)-5-(3-hydroxypropyl)-1H-imidazole

A solution of 11.2 g of 1-dimethylcarbamoyl-4-(3-trimethylsilyloxypropyl)-1H-imidazole and 12.49 g of p-bromobenzyl bromide in 110 ml of acetonitrile is refluxed for 24 h. The solution is cooled to 0° and ammonia gas is bubbled through the reaction mixture for 5 min. After reacting an additional 45 min at room temperature, the solvent is evaporated. The residue is taken up in 100 ml of 1N hydrochloric acid and extracted with 50 ml of ether. The aqueous phase is adjusted to pH 8 and extracted with ethyl acetate (5×50 ml). The organic extracts are washed with water, dried over sodium sulfate and evaporated. The resulting oil is chromatographed on 530 g of silica gel with ethyl acetate:methanol:saturated NH₄OH (90:5:5) to yield the title compound a) as an oil; NMR: $\delta$5.00 (s, 2H).

b) 1-(p-Bromobenzyl)-5-(3-chloropropyl)-1H-imidazole 1-(p-Bromobenzyl)-5-(3-hydroxypropyl)-1H-imidazole is treated with thionyl chloride analogous to the method described in example 1c) to give the title compound b).

EXAMPLE 18

5-(p-Cyanophenyl)-5,6,7,8-tetrahydroimidazo[1,5-a]pyridine

A solution of 2.01 g of 5-(p-formylphenyl)-5,6,7,8-tetrahydroimidazo[1,5-a]pyridine and 0.96 g of hydrazoic acid in 30 ml benzene is maintained by external cooling at room temperature, while 0.8 ml of concentrated sulfuric acid is added dropwise. The reaction mixture is stirred for 2 h and neutralized. The organic phase is separated, dried over sodium sulfate and evaporated to yield an oil which is chromatographed on silica gel with ethyl acetate to yield the title compound.

EXAMPLE 19

5-(p-Hydroxymethylphenyl)-5,6,7,8-tetrahydroimidazo[1,5-a]pyridine

A solution of 0.40 g of 5-(p-ethoxycarbonylphenyl)-5,6,7,8-tetrahydroimidazo[1,5-a]pyridine in 20 ml of methylene chloride is cooled to −70° under nitrogen and 4.0 ml of a 1.53M diisobutylaluminium hydride solution in toluene is added dropwise. The reaction mixture is allowed to warm to room temperature, quenched with 3.2 ml of methanol and 15 ml of water and filtered through Celite®. The layers are separated, the organic one is dried over sodium sulfate and evaporated to yield the title compound, m.p. 142°–145°.

EXAMPLE 20

5-(p-Formylphenyl)-5,6,7,8-tetrahydroimidazo[1,5-a]pyridine

A solution of 0.16 ml of dimethylsulfoxide in 16 ml of methylene chloride is cooled to −70° under nitrogen and 0.17 g of oxalyl chloride is added dropwise. The reaction mixture is stirred for 30 min and 0.24 g of 5-(p-hydroxymethylphenyl)-5,6,7,8-tetrahydroimidazo[1,5-a]pyridine in 4 ml of methylene chloride is added slowly. The reaction mixture is stirred for 2 h at −70°, 0.8 ml of triethylamine is added dropwise, and the reaction mixture is allowed to warm slowly to room temperature. The reaction mixture is diluted with 20 ml of methylene chloride, washed with water, dried over sodium sulfate and evaporated to yield the title compound which is purified by conversion to the fumaric acid salt, m.p. 131°.

EXAMPLE 21

5-(p-Cyanophenyl)-5-methylthio-5,6,7,8-tetrahydroimidazo[1,5-a]pyridine hydrochloride A solution of lithium diisopropylamide is prepared at 0° under nitrogen from 0.6 ml of n-butyllithium (2.5M) and 0.15 g of diisopropylamine in 5 ml of dry tetrahydrofuran and is transferred to 0.29 g of 5-(p-cyanophenyl)-5,6,7,8-tetrahydroimidazo-[1,5-a]pyridine in 10 ml of tetrahydrofuran at −78°. The reaction mixture is stirred for 30 min and 0.14 g of dimethyl disulfide is added dropwise. Cooling is discontinued after 30 min and the reaction mixture is allowed to warm to room temperature and quenched with 10 ml of saturated ammonium chloride solution. The layers are separated and the organic phase is washed with cold 1N hydrochloric acid. The aqueous phase is neutralized and extracted with ethyl acetate. The organic extracts are dried over sodium sulfate and evaporated to an oil which is chromatographed on silica gel with 5% isopropanol in ethyl acetate. The resulting oil is redissolved in acetone and treated with 0.1 ml of 4N ethereal hydrogen chloride to yield the title compound, m.p. 204°–205°.

EXAMPLE 22

5-(p-Cyanophenyl)-5-ethoxycarbonyl-5,6,7,8-tetrahydroimidazo[1,5-a]pyridine

In a manner analogous to that described in example 21, reaction of 5-(p-cyanophenyl)-5,6,7,8-tetrahydroimidazo[1,5-a]pyridine with ethyl chloroformate yields the title compound.

EXAMPLE 23

5-(p-Cyanophenyl)-5,6,7,8-tetrahydroimidazo[1,5-a]pyridine

A solution of 1.65 g of 5-(p-cyanophenyl)-5-ethoxycarbonyl-5,6,7,8-tetrahydroimidazo[1,5-a]pyridine in 10 ml of methanol containing 0.2 g of sodium hydroxide is stirred for 3 h at room temperature and 5 ml of 1N hydrochloric acid is added. The reaction mixture is refluxed for 1 h, cooled and evaporated. The residue is partitioned between water and ethyl acetate. The organic layer is separated, dried over sodium sulfate and evaporated to yield the title compound.

The starting material is prepared as follows:

A solution of 1.9 g of ethyl p-cyanophenylacetate in 50 ml of diglyme is added to a slurry of 0.48 g of sodium hydride (50% oil dispersion) in 10 ml of diglyme. The reaction mixture is stirred at room temperature for 2 h, cooled to 0° and 1.75 g of N-bromosuccinimide is added portionwise. The solvent is evaporated under high vacuum and the residue is chromatographed on 50 g of silica with ether to yield ethyl-α-bromo-p-cyanophenylacetate.

A solution of 97.0 g of 4-(3-trimethylsilyloxypropyl)-1H-imidazole-1-N,N-dimethyl-carboxamide and 72.0 g of ethyl-α-bromo-p-cyano-phenylacetate in 500 ml of acetonitrile is refluxed for 10 h. The solution is cooled to 0° in an ice bath and ammonia gas is bubbled in for a few minutes. The mixture is then evaporated in vacuo to give a residue which is dissolved in 500 ml of 1N hydrochloric acid.

The solution is allowed to stand at room temperature for 15 min and then is extracted with ether. The pH of the aqueous phase is adjusted to 9 with 50% sodium hydroxide and the mixture is then extracted with methylene chloride. The methylene chloride extracts are washed with water, dried over sodium sulfate and evaporated to give 1-(α-ethoxycarbonyl-p-cyanobenzyl)-1H-imidazole-5-propanol.

To a solution of 5.75 g of thionylchloride in 80 ml of methylene chloride is added 8.4 g of 1-(α-ethoxycarbonyl-p-cyanobenzyl)-1H-imidazole-5-propanol as a solid in portions. When addition is complete, the solution is refluxed for 1.5 h, cooled in ice and filtered to obtain 5-(3-chloropropyl)-1-(α-ethoxycarbonyl-p-cyanobenzyl)-1H-imidazole hydrochloride. The salt is partitioned between methylene chloride and saturated sodium bicarbonate. The organic extracts are washed with water, dried over sodium sulfate and evaporated to yield the free base.

A solution of 8.1 g of 5-(3-chloropropyl)-1-(α-ethoxycarbonyl-p-cyanobenzyl)-1H-imidazole in 50 ml of tetrahydrofuran is cooled to 0° in an ice bath. To this is added 8.0 g of potassium-t-butoxide as a solid in portions. The mixture is stirred at room temperature for 2 h, neutralized with 10% acetic acid and partitioned between methylene chloride and water. The organic layer is washed with water, dried over magnesium sulfate and evaporated to yield an oil which is dissolved in a small volume of acetone and neutralized with ethereal hydrogen chloride. The solid is collected to yield 5-(p-cyclophenyl)-5-ethoxycarbonyl-5,6,7,8-tetrahydroimidazo[1,5-a]pyridine.

EXAMPLE 24

5-(p-Cyanophenyl)-5,6,7,8-tetrahydroimidazo[1,5-a]pyridine

A solution of 2.13 g of 5-(p-aminophenyl)-5,6,7,8-tetrahydroimidazo[1,5-a]pyridine in 4 ml of concentrated hydrochloric acid and 10 ml of water is cooled in an ice-bath and a solution of 0.78 g of sodium nitrite in 2 ml of water is added slowly. The solution is added via dropping funnel to an ice cooled solution of 3.0 g of copper(I) cyanide in 10 ml of water, keeping the temperature between 30°–40°. The reaction mixture is heated on a steam bath for 1 h, cooled and brought to pH 9. The organic extracts are dried over sodium sulfate and evaporated and the residue is chromatographed on silica gel with ethyl acetate to yield the title compound.

EXAMPLE 25

5-(p-Aminophenyl)-5,6,7,8-tetrahydroimidazo[1,5-a]pyridine

A solution of 2.42 g of 5-(p-carboxyphenyl)-5,6,7,8-tetrahydroimidazo[1,5-a]pyridine in 100 ml of ethylene dichloride is treated with 6 ml of concentrated sulfuric acid. The reaction mixture is heated to 40° and 6 ml of hydrazoic acid (2M is ethylene dichloride) is added dropwise. When gas evolution has ceased, the reaction mixture is evaporated. The residue is redissolved in water and adjusted to pH 10. The aqueous phase is extracted with methylene chloride (3×30 ml). The organic extracts are dried over potassium carbonate and evaporated to yield the title compound.

EXAMPLE 26

Preparation of 10,000 tablets each containing 10 mg of the active ingredient:

| Formula: | |
|---|---|
| 5-(p-Cyanophenyl)-5,6,7,8-tetrahydroimidazo[1,5-a]pyridine | 100.00 g |
| Lactose | 2535.00 g |
| Corn starch | 125.00 g |
| Polyethylene glycol 6,000 | 150.00 g |
| Magnesium stearate | 40.00 g |
| Purified water | q.s. |

All the powders are passed through a screen with openings of 0.6 mm. Then the drug substance, lactose, magnesium stearate and half of the starch are mixed in a suitable mixer. The other half of the starch is suspended in 65 ml of water and suspension is added to the boiling solution of the polyethylene glycol in 260 ml of water. The paste formed is added to the powders, which are granulated, if necessary, with an additional amount of water. The granulate is dried overnight at 35°, broken on a screen with 1.2 mm openings and compressed into tablets, using concave uppers bisected.

Analogously tablets are prepared containing the other compounds disclosed and exemplified herein.

EXAMPLE 27

Preparation of 1,000 capsules each containing 20 mg of the active ingredient:

| Formula: | |
|---|---|
| 5-(p-Cyanophenyl)-5,6,7,8-tetrahydro- | 20.0 g |

| -continued | |
|---|---|
| Formula: | |
| imidazo[1,5-a]pyridine | |
| Lactose | 207.0 g |
| Modified starch | 80.0 g |
| Magnesium stearate | 3.0 g |

All the powders are passed through a screen with openings of 0.6 mm. Then the drug substance is placed in a suitable mixer and mixed first with the magnesium stearate, then with the lactose and starch until homogeneous. No. 2 hard gelatin capsules are filled with 310 mg of said mixture each, using a capsule filling machine.

Analogously capsules are prepared, containing the other compounds disclosed and exemplified herein.

EXAMPLE 29

A solution of 5-(p-hydroxymethylphenyl)imidazo[1,5-a]pyridine (0.52 g) in 10 ml of methylene chloride is refluxed with 5.2 g of activated manganese dioxide for 24 h. An additional 5.2 g of manganese dioxide is added and the reaction mixture is refluxed an additional 6 h, filtered, and the solvent is evaporated to yield 5-(p-formylphenyl)-imidazo[1,5-a]pyridine, m.p. 144°–146°.

EXAMPLE 29

A solution of 0.18 g of 5-(p-carboxyphenyl)imidazo[1,5-a]pyridine hydrochloride in 5 ml of thionyl chloride is refluxed for 30 min and evaporated to dryness. The resulting oil is redissolved in 10 ml of methylene chloride and ammonia is bubbled into the solution at 0° for 1 h. The solution is washed with water and dried over sodium sulfate. Evaporation yields 5-(p-carbamoylphenyl)imidazo[1,5-a]pyridine, m.p. 228°–230° (dec.).

EXAMPLE 30

A solution of 3.13 g of 4-[3-(4-tert-butylaminocarbonylphenyl)-3-chloroprop-1-yl]-1-tritylimidazole in 150 ml of acetonitrile is refluxed for 15 h, cooled and 150 ml of methanol is added. The reaction mixture is refluxed an additional 15 h and evaporated to dryness. The residue is partitioned between ether and water. The other layer is separated and washed with 1N HCl (2×15 ml). The combined aqueous extracts are adjusted to pH=8 and extracted with methylene chloride which is dried over sodium sulfate, filtered and evaporated to a white foam. The product is crystallized from ether to yield 1.30 g of 5H-5-(4-tert-butylaminocarbonylphenyl)-6,7-dihydropropyrrolo[1,2-c]imidazole, m.p. 136°–139°.

The starting material is prepared as follows:

a) A solution of 6.0 g of methyl 3-(1H-imidazol-4-yl)propionate and 11 ml of triethylamine in 31 ml of dimethylformamide is treated with a solution of 9.65 g of triphenylmethyl chloride in 110 ml of dimethylformamide for 2 h at room temperature under nitrogen. The reaction mixture is poured onto 700 g of ice, and the resulting solid is collected by filtration and recrystallized from ether to yield 13.83 g of methyl 3-(1-tritylimidazol-4-yl)propionate, NMR (CDCl$_3$) δ=2.75 (m, 4H), 3.05 (s, 3H), 6.5–7.5 (m, 17H).

b) A solution of 44.4 mmole of diisobutylaluminium hydride in 29 ml of toluene is added to a solution of 8.79 g of methyl 3-(1-tritylimidazol-4-yl)propionate in 175 ml of methylene chloride at −72° under nitrogen. After 5 min the reaction is quenched by adding 14 ml of methanol followed by 90 ml of water. The reaction mixture is allowed to warm to room temperature and is filtered through celite. The organic phase is separated, dried over sodium sulfate and evaporated to a yellow oil which is chromatographed on 280 g of silica with ether to yield 4.13 g of 3-(1-tritylimidazol-4-yl)propionaldehyde as an oil. IR (CDCl$_3$): 2830, 2740, 1730 cm$^{-1}$.

c) A solution of 25 mmoles of n-butyllithium in 10 ml of hexane is added dropwise to a solution of 3.19 g of N-tert-butyl 4-bromobenzamide in 250 ml of tetrahydrofuran at −70° under argon. After 30 min, a solution of 3.74 g of 3-(1-tritylimidazol-4-yl)propionaldehyde in 100 ml of tetrahydrofurane is added slowly. The reaction mixture is stirred at −70° for 30 min, allowed to warm to 25°, stirred at 25° for 2.5 h and quenched with excess saturated ammonium chloride solution. The aqueous layer is separated and extracted with methylene chloride (2×100 ml). The combined organic extracts are dried over sodium sulfate and evaporated. The residue is chromatographed on 220 g of silica with 5:1 ether:ethyl acetate to yield 4-[3-(4-tert-butylaminocarbonyphenyl)-3-hydroxyprop-1-yl]-1-tritylimidazole as an oil. IR (CH$_2$Cl$_2$): 1660 cm$^{-1}$.

d) A solution of 3.21 g of 4-[3-(4-tert-butylaminocarbonylphenyl)-3-hydroxyprop-1-yl]-1-tritylimidazole and 1.5 ml of thionyl chloride in 50 ml of methylene chloride is refluxed for 1 h, cooled and poured into 50 ml of ice-cold sodium bicarbonate solution. The organic phase is separated, dried over sodium sulfate and evaporated to yield 4-[3-(4-tert-butylaminocarbonylphenyl)-3-chloroprop-1-yl]-1-tritylimidazole as a white foam. NMR (CDCl$_3$): δ=1.45 (s, 9H), 4.30 (t, J=6.0 Hz, 2H).

EXAMPLE 31

A solution of 1.25 g of 5H-5-(4-tert-butylaminocarbonylphenyl)-6,7-dihydropyrrolo[1,2-c]imidazole in 10 ml of thionyl chloride is refluxed for 1 h, cooled and evaporated. The residue is redissolved in 10 ml of chloroform at 0° and 10 ml of ice-cold conc. ammonium hydroxide is slowly added. The aqueous layer is separated, extracted with chloroform (3×20 ml) and the combined organic extracts are dried over sodium sulfate. Filtration, evaporation and chromatography on 45 g of silica with 5% ammonium hydroxide in ethyl acetate, provides an oil which is treated with 1 molar equivalent of ethereal hydrogen chloride to yield 0.5 g of 5H-5-(4-cyanophenyl)-6,7-dihydropyrrolo[1,2-c]imidazole, m.p. 227°–228°.

EXAMPLE 32

A solution of 1.29 g of 5H-5-(4-tert-butylaminocarbonylphenyl)-6,7,8,9-tetrahydroimidazo[1,5-a]azepine in 10 ml of thionyl chloride is refluxed for 1 h, cooled and evaporated. The residue is partitioned between methylene chloride and ice-cold sodium bicarbonate solution. The aqueous layer is separated and extracted with methylene chloride (3×15 ml). The combined organic layers are dried over sodium sulfate and evaporated. The resulting oil is chromatographed on 26 g of silica with 5% methanol in methylene chloride. The product is treated with one molar equivalent of fumaric acid in ethanol to yield 5H-5-(4-cyanophenyl)-6,7,8,9-tetrahydroimidazo[1,5-a]azepine, m.p. 153°–155°.

The starting material is made from ethyl 5-(1-tritylimidazo-4-yl)-1-pentanoate in an identical manner to the preparation of 5H-5-(4-tert-butylaminocarbonylphenyl)-6,7-dihydropyrrolo[1,2-c]imidazole from ethyl 3-(1-tritylimidazol-4-yl)propionate which is prepared as follows:

a) A solution of 5.6 ml of diisopropylamine in 150 ml of tetrahydrofuran at −70° under nitrogen is treated with 14.5 ml of 2.5M n-butyllithium for 30 min and 7.2 ml of triethylphosphonoacetate is added dropwise. After 30 min, a solution of 10.09 g of 3-(1-tritylimidazol-4-yl)propionaldehyde in 50 ml of tetrahydrofuran is added slowly. The reaction mixture is allowed to warm slowly to room temperature, stirred for 15 h and quenched with excess saturated ammonium chloride solution. The aqueous layer is separated and extracted with ethyl acetate (2×50 ml). The combined organic extracts are dried over sodium sulfate and evaporated to an oil (15.35 g), which is chromatographed on 430 g of silica with ether to yield 9.61 g of ethyl 5-(1-tritylimidazol-4-yl)-1-pent-2-enoate, m.p. 86°-88°.

b) A solution of 9.20 g of ethyl 5-(1-tritylimidazol-4-yl)-1-pent-2-enoate in 460 ml of anhydrous ethanol is hydrogenated with 1.88 g of 10% palladium on charcoal at atmospheric pressure for 20 min. The catalyst is removed by filtration through celite. Evaporation provides a solid which is recrystallised from hexane to yield 8.64 g of ethyl 5-(1-tritylimidazol-4-yl)-1-pentanoate, m.p. 84°-86°.

EXAMPLE 33

A solution of 1.27 g of ethyl 5-[1-(4-cyanobenzyl)imidazol-5-yl]-1-pent-2-enoate in 27 ml of tetrahydrofuran at 5° under nitrogen is treated with 0.52 g of potassium tert-butoxide. The reaction mixture is stirred at 5° for 2 h and 10 ml of 1N hydrochloric acid is added. The layers are separated. The organic phase is extracted with 1N hydrochloric acid (2×10 ml). The combined aqueous layers are extracted with ether, adjusted to pH=8 and extracted with methylene chloride (3×15 ml). The organic phase is dried and evaporated to yield the product which is treated with one molar equivalent of ethereal hydrogen chloride. The resulting solid is recrystallized from acetone to yield 5-(4-cyanophenyl)-6-ethoxycarbonylmethyl-5,6,7,8-tetrahydroimidazo[1,5-a]pyridine. m.p. 126°-127°.

The starting material is prepared as follows:

a) A solution of 2.9 ml of dry dimethylsulfoxide in 250 ml of methylene chloride is cooled to −78° under nitrogen and 2.1 ml of oxalyl chloride is added dropwise. After 30 min at −78°, a solution of 5.0 g of 3-[1-(4-cyanobenzyl)imidazol-5-yl]-1-propanol in 18 ml of dimethylsulfoxide is added slowly. The reaction mixture is stirred for 2 h and 10.4 ml of triethylamine is added. Then it is allowed to warm to room temperature and is washed with water (4×100 ml). The organic phase is dried over sodium sulfate and evaporated to yield 4.13 g of 3-[1-(4-cyanobenzyl)imidazol-5-yl]-1-propionaldehyde. IR ($CH_2Cl_2$): 2750, 2250, 1732 $cm^{-1}$.

b) A solution of 23 mmoles of lithium diisopropylamide, from 3.2 ml of diisopropylamine and 9.2 ml of 2.5M n-butyllithium, in 170 ml of tetrahydrofuran at 0° under nitrogen, is cooled to −78° and 4.2 ml of triethylphosphonoacetate is added dropwise. After 30 min, a solution of 4.1 g of 3-[1-(4-cyanobenzyl)imidazol-5-yl]-1-propionaldehyde in 30 ml of tetrahydrofuran is added slowly. The reaction mixture is stirred at −78° for 2 h, allowed to warm to room temperature and stirred an additional 15 h before being quenched with excess saturated ammonium chloride solution. The aqueous layer is separated and extracted with ethyl acetate (2×50 ml). The combined organic layers are dried over sodium sulfate and evaporated to a yellow oil which is chromatographed on 20 g of silica gel using ether, ethyl acetate (1:1) as eluant to yield 3.56 g of ethyl 5-[1-(4-cyanobenzyl)imidazol-5yl]-1-pent-2-enoate. IR ($CH_2Cl_2$): 2240, 1720 $cm^{-1}$.

EXAMPLE 34

A solution of 0.21 g of 5-(4-cyanophenyl)-6-ethoxycarbonylmethyl-5,6,7,8-tetrahydroimidazo[1,5-a]pyridine hydrochloride in 1.2 ml of ethanol and 1.2 ml of 1N sodium hydroxide is stirred at room temperature for 15 h, evaporated and the residue is redissolved in water. The aqueous phase is extracted with ethyl acetate, adjusted to pH=2, reextracted, neutralized and evaporated. The residue is triturated with tetrahydrofuran. The organic phase is treated with ethereal hydrogen chloride and 0.12 g of 5-(4-cyanophenyl)-6-carboxymethyl-5,6,7,8-tetrahydroimidazo[1,5-a]pyridine, m.p. 209°-211°, is collected.

EXAMPLE 35

A solution of 0.80 mmoles of lithium diisopropylamide, prepared from 0.12 ml of diisopropylamine and 0.32 ml of 2.5M n-butyllithium in 6 ml of tetrahydrofuran at 0°, is slowly added to a solution of 0.17 g of 5-(4-cyanophenyl)-5,6,7,8-tetrahydroimidazo[1,5-a]pyridine in 2 ml of tetrahydrofuran at −79°. After 0.5 h, 0.1 ml of benzyl bromide is added dropwise. The reaction mixture is stirred for an additional 1 h, quenched with 5 ml of water, made acidic with 1N hydrochloric acid, diluted with 20 ml of ether and the layers are separated. The aqueous phase is adjusted to pH=7, extracted with ethyl acetate (3×15 ml) and the organic extracts are dried over sodium sulfate. Filtration and evaporation produces a foam which is treated with one molar equivalent of ethereal hydrogen chloride to yield 5-benzyl-5-(4-cyanophenyl)-5,6,7,8-tetrahydroimidazo[1,5-a]pyridine hydrochloride, m.p. 249°-251°.

EXAMPLE 36

7-(p-Cyanophenyl)-5,6,7,8-tetrahydroimidazo[1,5-a]pyridine hydrochloride, m.p. 253°-254°, is prepared by a similar sequence of transformation from 4-(p-ethoxycarbonylphenyl)pyridine as described in examples 4, 8–10 and 7.

EXAMPLE 37

7-(p-Carbamoylphenyl)-5,6,7,8-tetrahydroimidazo[1,5-a]pyridine fumarate, m.p. 193°-195°, is prepared by a similar sequence of transformations from 4-(p-ethoxycarbonylphenyl)pyridine as described in examples 4 and 8–10.

EXAMPLE 38

A solution of 1.65 g of 5-(p-cyanophenyl)-3-ethoxycarbonyl-5,6,7,8-tetrahydroimidazo[1,5-a]pyridine in 10 ml of methanol containing 0.2 g of sodium hydroxide is stirred for 3 h at room temperature. The solution is warmed to reflux and 5 ml of 1N hydrochloric acid is added. After 1 h the reaction mixture is cooled and evaporated. The residue is partitioned between water and ethyl acetate. The organic layer is separated, dried over sodium sulfate and evaporated to yield 5-(p-cyanophenyl)-5,6,7,8-tetrahydroimidazo[1,5-a]pyridine, m.p. 128°-131°.

The starting material is prepared as follows:

A solution of 2.0 g of 2-aminomethyl-6-(p-cyanophenyl)pyridine in 20 ml of methylene chloride at −15° under nitrogen is treated with 1.4 g of ethyl oxalyl chloride. The reaction mixture is allowed to warm to room temperature over 2 h and the solvent is evaporated. The residue is dissolved in 30 ml of phosphorus oxychloride, the reaction mixture is refluxed for 15 h, and evaporated to dryness. The residue is partitioned between methylene chloride and sodium bicarbonate solution. The organic phase is separated, dried over sodium sulfate and evaporated to yield an oil which is chromatographed on 100 g of silica gel with ethyl acetate as eluant to provide 5-(p-cyanophenyl)-3-ethoxycarbonyl-imidazo[1,5-a]pyridine.

A solution of 1.1 g of 5-(p-cyanophenyl)-3-ethoxycarbonyl-imidazo[1,5-a]pyridine in 30 ml of ethanol is hydrogenated with 0.1 g of 10% Pd on charcoal at 1 bar for 2 h, filtered and evaporated to dryness. The resulting oil is partitioned between water and ethyl acetate. The organic phase is separated, dried over sodium sulfate and evaporated. The residue is chromatographed on 40 g of silica gel with ethyl acetate to yield 5-(p-cyanophenyl)-3-ethoxycarbonyl-5,6,7,8-tetrahydroimidazo[1,5-a]pyridine.

EXAMPLE 39

A solution of 0.24 g of 1-(p-cyanophenyl)-4-(4-imidazolyl)-1-butanone in 20 ml of methanol at room temperature is treated with 0.2 g of sodium cyanoborohydride. The pH is adjusted and maintained at 5.5–6.0 by addition of concentrated hydrochloric acid. The reaction mixture is stirred for 2 h, adjusted to pH 2, and evaporated to dryness. The residue is taken up in methylene chloride and washed with saturated sodium bicarbonate. The organic layer is dried over sodium sulfate and evaporated to yield 5-(p-cyanophenyl)-5,6,7,8-tetrahydroimidazo[1,5-a]pyridine.

The starting material is prepared as follows:

6.95 g of N-tert-butyl-p-bromobenzamide is dissolved in 175 ml of tetrahydrofuran at −70° under nitrogen and 20.1 ml of n-butyllithium (2.7M) is added dropwise. After 30 min, a solution of 5.35 g of 4-(1-trityl-4-imidazolyl)-butanoic acid in 10 ml of tetrahydrofuran is added slowly. The reaction mixture is allowed to warm slowly to room temperature and 20 ml of an aqueous ammonium chloride solution is added. The organic layer is separated, dried over sodium sulfate and evaporated to yield 1-(p-N-tert-butylaminocarbonylphenyl)-4-(1-trityl-4-imidazolyl)-1-butanone.

A solution of 0.5 g of 1-(p-N-tert-butylaminocarbonylphenyl)-4-(1-trityl-4-imidazolyl)-1-butanone in 20 ml of thionyl chloride is refluxed for 3 h and poured into 100 ml of ice-water. The aqueous phase is extracted with ether (3×20 ml), adjusted to pH=10 and reextracted with methylene chloride. The organic phase is dried and evaporated to yield 1-(p-cyanophenyl)-4-(4-imidazolyl)-1-butanone.

EXAMPLE 40

Racemic 5-(p-cyanophenyl)-5,6,7,8-tetrahydroimidazo[1,5-a]pyridine hydrochloride is applied, in 20 mg aliquots, to a 4.6×250 mm beta-cyclodextrin bonded silica gel column using 7:3 water:methanol as the eluant at a flow rate of 0.8 ml/min. The separate fractions are evaporated under vacuum to yield (−)-5-(p-cyanophenyl)-5,6,7,8-tetrahydroimidazo[1,5-a]pyridine, $[\alpha]_D^{25} = -89.2°$ and (+)-5-(p-cyanophenyl)-5,6,7,8-tetrahydroimidazo[1,5-a]pyridine, $[\alpha]_D^{25} + 85.02°$. Both compound are separately dissolved in acetone and treated with 1 molar equivalent of ethereal hydrogen chloride to yield the hydrochloride salts, m.p. 82°–83° (amorphous) and m.p. 218°–220°, respectively.

EXAMPLE 41

In a manner analogous to the previous examples, also the following compounds can be prepared:
- 5-(m-cyanophenyl)-5,6,7,8-tetrahydroimidazo[1,5-a]pyridine,
- 5-(o-cyanophenyl)-5,6,7,8-tetrahydroimidazo[1,5-a]pyridine,
- 5H-5-(3-cyanophenyl)-6,7-dihydropyrrolo[1,2-c]imidazole,
- 5H-5-(2-cyanophenyl)-6,7-dihydropyrrolo[1,2-c]imidazole,
- 5-(m-cyanophenyl)imidazo[1,5-a]pyridine,
- 5-(o-cyanophenyl)imidazo[1,5-a]pyridine,
- 6-(p-cyanophenyl)-5,6,7,8-tetrahydroimidazo[1,5-a]pyridine,
- 8-(p-cyanophenyl)-5,6,7,8-tetrahydroimidazo[1,5-a]pyridine.

What is claimed is:

1. A method of preparing a compound of formula I*

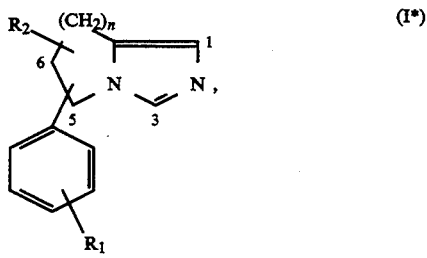

wherein n denotes 2; $R_1$ represents cyano or halogen; $R_2$ represents hydrogen; and wherein the substituents $C_6H_4$-$R_1$ and $R_2$ are attached at the 5-position; or a pharmaceutically acceptable salt thereof; which comprises a) condensing a compound of the formula

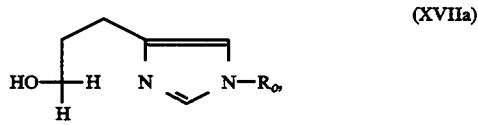

wherein $R_o$ is an NH blocking group and the hydroxy group is protected by a hydroxy protecting group, with a compound of the formula XVIIIa

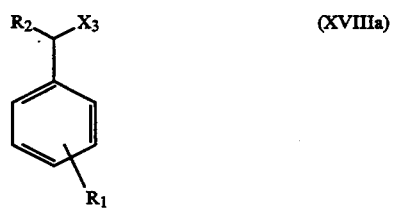

wherein $R_1$ represents cyano or halogen, $R_2$ represents lower alkoxycarbonyl or hydrogen, and $X_3$ is a leaving group selected from halogen, hydroxy esterified with a carboxylic acid and hydroxy esterified with a sulfonic acid, and removing protecting groups, to obtain a compound of formula Vb

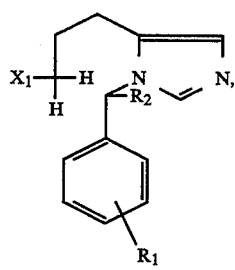

(Vb)

wherein $R_1$ and $R_2$ are as defined above and $X_1$ represents hydroxy;

(b) converting last said compound of formula Vb to a compound of formula Vb wherein $X_1$ is a leaving group selected from halogen, hydroxy esterified with a carboxylic acid and hydroxy esterified with a sulfonic acid;

(c) cyclizing last said compound of formula Vb in the presence of a base to corresponding compound of formula I*; and (d) if $R_2$ in resulting compound of formula I* represents lower alkoxycarbonyl, hydrolyzing and decarboxylating the said compound of formula I* to the corresponding compound wherein $R_2$ represents hydrogen; and (e) if desired converting the resulting compound of formula I* to a pharmaceutically acceptable salt thereof.

2. A method according to claim of preparing 5-(4-cyanophenyl)-5,6,7,8-tetrahydroimidazo[1,5-a]pyridine or a pharmaceutically acceptable salt thereof.

3. A method of preparing 5-(4-cyanophenyl)-5,6,7,8-tetrahydroimidazo[1,5-a]pyridine or a pharmaceutically acceptable salt thereof which comprises:

a) protecting the NH and hydroxy groups in 4-(3-hydroxypropyl)-imidazole and condensing a resulting compound of the formula

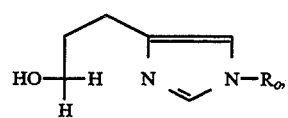

(XVIIa)

wherein $R_o$ is a di-lower alkylated carbamoyl NH blocking group and the hydroxy group is protected by a tri-lower alkylsilyl hydroxy protecting group, with a compound of the formula XVIIIa

(XVIIIa)

wherein $R_1$ represents p-cyano, $R_2$ represents hydrogen and $X_3$ is a halogen or sulfonyloxy leaving group, and removing protecting groups, to obtain a compound of formula Vb

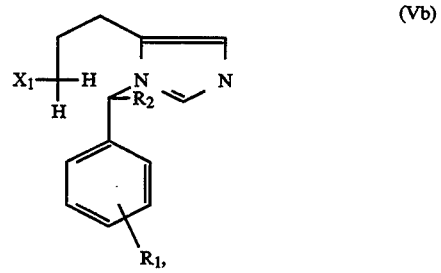

(Vb)

wherein $R_1$ and $R_2$ are as defined above and $X_1$ represents hydroxy;

(b) converting last said compound to a compound of formula Vb wherein $X_1$ is a halogen or sulfonyloxy leaving group;

(c) cyclizing last said compound of formula Vb in the presence of a base; and (d) if desired converting the resulting 5-(4-cyanophenyl)-5,6,7,8-tetrahydroimidazo[1,5-a]pyridine to a pharmaceutically acceptable salts thereof.

4. A method according to claim 1 wherein $R_2$ in formula XVIIIa and Vb represents lower alkoxycarbonyl and the resulting product is hydrolyzed and decarboxylated.

* * * * *